(12) United States Patent
Zaleski et al.

(10) Patent No.: US 6,514,995 B1
(45) Date of Patent: Feb. 4, 2003

(54) ENEDIYNE COMPOUNDS AND METHODS RELATED THERETO

(75) Inventors: Jeffrey M. Zaleski, Bloomington, IN (US); Diwan Singh Rawat, Bloomington, IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/962,388

(22) Filed: Sep. 25, 2001

Related U.S. Application Data

(60) Provisional application No. 60/235,022, filed on Sep. 25, 2000.

(51) Int. Cl.$^7$ ..................... A61K 31/44; C07D 401/12

(52) U.S. Cl. ........................ 514/332; 546/2; 546/264

(58) Field of Search ................. 546/2, 264; 514/332

(56) References Cited

U.S. PATENT DOCUMENTS

| | | |
|---|---|---|
| 5,371,199 A | 12/1994 | Therien et al. |
| 5,986,090 A | 11/1999 | Therien et al. |
| 6,043,237 A | 3/2000 | Meadows et al. |

OTHER PUBLICATIONS

Rawat, D.S. et al. : Mg2+ –induced thermal enediyne cyclization at ambient temperature. J. Am. Chem. Soc. vol. 123, pp. 9675–9676, 2001.*
Nicolaou et al. "Molecular Design and Chemical Synthesis of Potent Enediynes," Chem. Abst., 117, Abstract 233658v and Abstract 233659w, 835 (1992).
U.S. patent application Ser. No. 09/913,924, Zaleski et al., filed Aug. 20, 2001.
Ali et al., "Metal Complexes as Photo– and Radiosensitizers," Chem. Rev., 99, 2379–2450 (1999).
Basak et al., "The Synthesis and Reactivity of Novel Azetidinyl Enediynes," Chem. Commun., 749–750 (1996).
Bergman, "Reactive 1,4–Dehydroaromatics," Accounts of Chemical Research, 6, 25–31 (1973).
Bonadies et al., "Vanadium Phenolates as Models for Vanadium in Biological Systems. 1. Synthesis, Spectroscopy, and Electrochemistry of Vanadium Complexes of Ethylenebis [(o–hydroxyphenyl)glycine] and its Derivatives," J. Am. Chem. Soc., 108, 4088–4095 (1986).
Bonnett, "Photosensitizers of the Porphyrin and Phtalocyanine Series for Photodynamic Therapy," Chem. Soc. Reviews, 24, 19–33 (1995).
Boyle et al., "Structure and Biodistribution Relationships of Photodynamic Sensitizers," Photochemistry and Photobiology, 64 (3), 469–485 (1996).
Branca et al., "Formation and Structure of the Tris(catecholato)vanadate(IV) Complex in Aqueous Solution," Inorg. Chem., 29, 1586–1589 (1990).

Chapman et al., "9,10–Dehydroanthracene. A Derivative of 1,4–Dehydrobenzene," J. Am. Chem. Soc., 98 (18), 5703–5705 (1976).
Christner et al., "Unmasking the Chemistry of DNA Cleavage by the Esperamicins: Modulation of 4'–Hydrogen Abstraction and Bistranded Damage by the Fucose– Anthranilate Moiety," J. Am. Chem. Soc., 114, 8763–8767 (1992).
Churcher et al., "Synthesis of the Enediyne Aglycon (±)–Calicheamicinone," J. Am. Chem. Soc., 120, 3518–3519 (1998).
Cummings et al., "Luminescent Platinum (II) Complexes of Quinoxaline–2,3–dithiolate," Inorg. Chem., 34, 2007–2014 (1995).
Cummings et al., "Tuning the Excited–State Properties of Platinum (II) Diimine Dithiolate Complexes," J. Am. Chem. Soc., 118, 1949–1960 (1996).
Dai et al., "Synthesis and DNA Clavage Study of a 10–Membered Ring Enediyne Formed via Allylic Rearrangement," J. Org. Chem., 64, 682–683 (1999).
Evenzahav et al., "Photochemical Rearragement of Endiynes: Is a "Photo–Bergman" Cyclization a Possibility?" J. Am. Chem. Soc., 120, 1835–1841 (1998).
Funk et al., "Photochemical Cycloaromatization Reactions of ortho–Dialkynylarenes: A New Class of DNA Photocleaving Agents," J. Am. Chem. Soc., 118, 3291–3292 (1996).
Golik et al., "Esperamicins, a Novel Class of Potent Antitumor Antibiotics. 2. Structure of Esperamicin X," J. Am. Chem. Soc., 109, 3461–3462 (1987).
Golik et al., "Esperamicns, a Novel Class of Potent Antitumor Antibiotics. 3. Structures of Esperamicins A1, A2, and A1b," J. Am. Chem. Soc., 109, 3462–3464 (1987).
Hangeland et al., "Specific Abstraction of the 5'(S)– and 4'–Deoxyribosyl Hydrogen Atoms from DNA by Calicheamicin $\gamma_1$," J. Am. Chem. Soc., 114, 9200–9202 (1992).

(List continued on next page.)

Primary Examiner—Charanjit S. Aulakh
(74) Attorney, Agent, or Firm—Leydig Voit & Mayer, Ltd.

(57) ABSTRACT

The invention provides novel tetradentate enediyne ligands that are themselves thermally stable, yet react at about room temperature or slightly higher upon addition of metal ions or under photothermal conditions. In another aspect of the invention, a method of treating a disorder in a mammal comprising administering a therapeutically effective amount of a compound or composition is provided. In addition, the free ligand can be delivered to the mammal prior to complexation to metals, such that the ligand is exposed to a metal in the body and forms a metal complex in vivo. Furthermore, a metal complex of the invention can be administered to the mammal such that the complex exchanges the first metal center with another endogenous metal in order to form a second metal complex in vivo. The second metal complex is capable of forming a benzenoid diradical under physiological conditions and/or under photothermal conditions.

35 Claims, 6 Drawing Sheets-

OTHER PUBLICATIONS

Holmes et al., "Models for the Binding Site in Bromoperoxidase: Mononuclear Vanadium (V) Phenolate Complexes of the Hydridotris(3,5-dimethylpyrazolyl)borate Ligand," *Inorg. Chem.*, 30, 1231–1235 (1991).

Kaneko et al., "Photochemical Cycloaromatization of Non-Benzenoid Enediynes," Angew. Chem. Int. Ed., 38 (9), 1267–1268 (1999).

Kim et al., "Rapid Bergman Cyclization of 1,2-Diethynylheteroarenes," *J. Org. Chem.*, 63, 8229–8234 (1998).

Konig et al., "Activation of Macrocyclic Biaryl-Enediynes by Metal Ion Coordination," *Angew. Chem. Int. Ed. Engl.*, 34 (22), 2538–2540 (1995).

Konig et al., "Synthesis, Structure, and Reactivity of Enediyne Macrocycles," *J. Org. Chem.*, 61, 4258–4261 (1996).

Kusakabe et al., "Conformation-Selective DNA Strand Breaks by Dynemicin: A Molecular Wedge into Flexible Regions of DNA," *Biochemistry*, 32, 11669–11675 (1993).

Lee et al., "Calicheamicins, a Novel Family of Antitumor Antibiotics. 4. Structure Elucidation of Calicheamicins $\beta_1^{Br}$, $\gamma_1^{Br}$, $\alpha_2^I$, $\alpha_3^I$, $\beta_1^I$, $\gamma_1^I$, and $\delta_1^I$," *J. Am. Chem. Soc.*, 114, 985–997 (1992).

Leet et al., "Chemistry and Structure Elucidation of the Kedarcidin Chromophore," *J. Am. Chem. Soc.*, 115, 8432–8443 (1993).

Li et al., "Vanadium Complexes of the Tridentate Schiff Base Ligand N-Salicylidene-N'- (2-hydroxyethyl)ethylenediamine: Acid-Base and Redox Conversion between Vanadium (IV) and Vanadium (V) Imino Phenolates," *Inogr. Chem.*, 27, 4657–4664 (1988).

Lockhart et al., "Evidence for the Reactive Spin State of 1,4-Dehydrobenzenes," *J. Am. Chem. Soc.*, 103, 4091–4096 (1981).

Magnus et al., "Synthetic and Mechanistic Studies on Esperamicin $A_1$ and Calicheamicin $\gamma_1$. Molecular Strain Rather Than $\pi$-Bond Proximity Determines the Cycloaromatization Rates of Bicyclo[7.3.1] Enediynes," *J. Am. Chem. Soc.*, 112, 4986–4987 (1990).

Maier, "Design of Enediyne Prodrugs," *Synlett*, 13–26 (1995).

Marthur et al., "Cytosine Methylation Enhances DNA Damage Produced by Groove Binding and Intercalating Enediynes: Studies with Esperamicins A1 and C," *Biochemistry*, 36, 14868–14873 (1997).

Minami et al., "Structure of an Aromatization Product of C-1027 Chromophore," *Tetrahedron Letters*, 34 (16), 2633–2636 (1993).

Myers et al., "Design and Synthesis of a System of Enediyne Formation by Anthraquinone Reductive Activation", *J. Am. Chem. Soc.*, 114, 5859–5860 (1992).

Myers et al., "Total Synthesis of (+)-Neocazinostatin Chromophore," *J. Am. Chem. Soc.*, 120, 5319–5320 (1998).

Kappen et al., "Replication Block by an Enediyne Drug-DNA Deoxyribose Adduct," *Biochemistry*, 38, 235–242 (1999).

Nicolaou et al., "Cyclic conjugated Enediynes Related to Calicheamicins and Esperamicins: Calculations, Synthesis, and Properties," *J. Am. Chem. Soc.*, 110, 4866–4868 (1988).

Nicolaou et al., "Synthesis and Chemistry of Dynemicin A Models," *J. Am. Chem. Soc.*, 113, 3106–3114 (1991).

Nicolaou et al., "Enediyne Compounds equipped with Acid-, Base- and Photo-Sensitive Triggering Devices. Chemical Simulation of the Dynemicin A Reaction Cascade," *Angew. Chem. Int. Ed. Engl.*, 30 (8), 1032–1036 (1991).

Nicolaou et al., "Design, Synthesis, and Study of Simple Monocyclic Conjugated Enediynes. The 10-Membered Ring Enediyne Moiety of the Enediyne Anticancer Antibiotics," *J. Am. Chem. Soc.*, 114, 7360–7371 (1992).

Nicolau et al., "Redox-Controlled Bergman Cycloaromatizations. Designed Enediynes with DNA-Cleaving Properties and Antitumor Activity," *J. Am. Chem. Soc.*, 114, 9279–9282 (1992).

Nicolaou et al., " Chemistry and Biology of Natural and Designed Enediynes," *Proc. Natl. Acad. Sci. USA*, 90, 5881–5888 (1993).

O'Brien et al., "Action Spectra of the Antileukemic and Antiviral Activities of Merocyanine 540," *Photochemistry and Photobiology*, 54 (5), 851–854 (1991).

Oseroff et al., "Strategies for Selective Cancer Photochemotherapy; Antibody-Targeted and Selective Carcinoma Cell Photolysis," *Photochemistry and Photobiology*, 46 (1), 83–96 (1987).

Pandey et al., "Porphyrin Dimers as Photosensitizers in Photodynamic Therapy," *J. Med. Chem.*, 33, 2032–2038 (1990).

Pandey et al., "Synthesis, Photophysical Properties, in Vivo Photosensitizing Efficacy, and Human Serum Albumin Binding Properties of Some Novel Bacteriochlorins," *J. Med. Chem.*, 40, 2770–2779 (1997).

Ramkumar et al., "Cyclization of Enediyne Radical Cations through Chemical, Photochemical, and Electrochemical Oxidation: The Role of State Symmetry," *J. Org. Chem.*, 61, 2247–2250 (1996).

Ressler et al., "Creating New Photosensitizers for Cancer Therapy," *Chemtech*, 28 (3), 39–45 (1998).

Schreiner, "Cyclic Enediynes: Relationship between Ring Size, Alkyne Carbon Distance, and Cyclization Barrier," *Chem. Commun.*, 483–484 (1998).

Schreiner, "Monocyclic Enediynes: Relationships between Ring Sizes, Alkyne Carbon Distances, Cyclization Barriers, and Hydrogen Abstraction Reactions. Sunglet-Triplet Separtions of Methyl-Subsitutted $\rho$-Benzynes," *J. Am. Chem. Soc.*, 120, 4184–4190 (1998).

Sessler et al., "Texaphyrins: Synthesis and Applications," *Acc. Chem. Res.*, 27, 43–50 (1994).

Shain et al., "The Synthesis and Reactivity of a Novel 10-Membered Azaenediyne," *Tetrahedron Letters*, 38 (34), 6067–6070 (1997).

Shair et al., "The Total Synthesis of Dynemicin A Leading to Development of a Fully Contained Bioreductively Activated Endiyne Prodrug," *J. Am. Chem. Soc.*, 118, 9509–9525 (1996).

Shiraki et al., "Visible Light Induced DNA Cleavage by the Hybrid Antitumor Antibiotic Dynemicin A," *Biochemistry*, 29, 9795–9798 (1990).

Smith et al., "The Enediyne Antibiotics," *Journal of Medicinal Chemistry*, 39 (11), 2103–2117 (1996).

Sugiura et al., "DNA Intercalation and Cleavage of an Antitumor Antibiotic Dynemicin that Contains Anthracycline and Enediyne Cores," *Proc. Natl. Acad. Sci. USA, 87*, 3831–3835 (1990).

Turro et al., "Photochemical Analogue of the Bergman Cycloaromatization Reaction," *Tetrahedron Letters, 35* (44) 8089–8092 (1994).

Warner et al., "Controlled Acceleration and Inhibition of Bergman Cyclization by Metal Chlorides," *Science, 269*, 814–816 (1995).

Wells, "Cancer Gets the Red Light. Pharmacyclics, Inc.," *Chemistry & Biology, 4* (10), 775–776 (1997).

Wender et al., "A Photochemically Triggered DNA Cleaving Agent: Synthesis, Mechanistic and DNA Cleavage Studies on a New Analog of the Antitumor Antibiotic Dynemicin," *J. Org. Chem., 58* (22), 5867–5869 (1993).

Wisniewski Grissom et al., "Determination of the Activation Parameters for the Bergman Cyclization of Aromatic Enediynes," *J. Org. Chem., 59*, 5833–5835 (1994).

Xi et al., "Mechanistic Studies on the Base–Catalyzed Transformation of Neocarzinostatin Chromophore: Roles of Bulged DNA," *Biochemistry, 38*, 4342–4354 (1999).

Xu et al., "Mechanism of Formation of Novel Covalent Drug DNA Interstrand Cr0ss–Links and Monoadducts by Enediyne Antitumor Antibiotics," *Biochemistry, 36*, 14975–14984 (1997).

Xu et al., "DNA Damage Produced by Enediynes in the Human Phosphoglycerate Kinase Gene in Vivo: Esperamicin A1 as a Nucleosome Footprinting Agent," *Biochemistry, 37*, 1890–1897 (1998).

Zein et al., "Calicheamicin $\gamma_1{}^I$: An Antitumor Antibiotic That Cleaves Double–Stranded DNA Site Specifically," Science, 240, 1198–1201 (1988).

Zein et al., "Exclusive Abstraction of Nonexchangeable Hydrogens from DNA by Calicheamicin γ1," *J. Am. Chem. Soc., 111*, 6888–6890 (1989).

Zein et al., "Calicheamicin $\gamma_1{}^I$ and DNA: Molecular Recognition Process Responsible for Site–Specificity," *Science, 244*, 697–699 (1989).

\* cited by examiner

Reagents and conditions:

(i) CH₂Cl₂, RT, 2.5 h, 75%; (ii) MeOH, NaBH₄, RT, 1 h, 84%; (iii) MeOH, MgCl₂, 0 °C, 8 h, 70%; (iv) MeOH, 1,4-CHD, RT; (v) NaBH₄, 5-10 °C, DMF, EDTA, CH₂Cl₂.

ENEDIYNE COMPOUNDS AND METHODS RELATED THERETO

CROSS-REFERENCE TO RELATED PATENT APPLICATIONS

This patent application claims the priority of U.S. Provisional Patent Application No. 60/235,022, filed Sep. 25, 2000, the contents of which are hereby incorporated by reference.

STATEMENT REGARDING FEDERALLY SPONSORED RESEARCH AND DEVELOPMENT

This invention was made in part with Government support under Grant Number R01 GM62541-01A1 awarded by the National Institutes of Health. The Government may have certain rights in this invention.

FIELD OF THE INVENTION

This invention pertains to tetradentate enediyne ligands and associated metal complexes, and their use in the treatment of cancers and infectious diseases.

BACKGROUND OF THE INVENTION

The potent antitumor activity of the enediyne natural product antibiotics such as calicheamicin, dynemicin, esperamicin, and neocarzinostatin has fostered interest in the development of simple enediynes with low thermal barriers to formation of the lethal 1,4-benzenoid diradical intermediate (see, e.g., Nicolaou, et al., *Angew. Chem., Int. Ed. Engl.* 1991, 30, 1387; Lee, et al., *J. Am. Chem. Soc.* 1987, 109, 3466; Konishi, et al., *J. Am. Chem. Soc.* 1990,112, 3715; Golik, et al., *J. Am. Chem. Soc.* 1987, 109, 3461; Edo, et al., *Tet. Lett.*, 1985, 26, 331). Such benzenoid diradicals are thought to be capable of cleaving DNA by H-atom abstraction. Benzenoid 1,4-diradicals can be formed via Bergman cyclization of a suitable enediyne.

To this end, carbocyclic enediyne frameworks, and more recently, novel metalloenediyne structures, have been described (see, e.g., commonly assigned published PCT/US00/04915, the entire contents of which are hereby incorporated by reference; Nicolaou, et al., *J. Am. Chem. Soc.* 1992, 114, 7360; Warner, et al., *Science* 1995, 269, 814; König, et al., *J. Org. Chem.* 1996, 61, 5258; Basak, et al., *J. Chem. Soc., Perkin Trans* 1 2000, 1955; Coalter, et al., *J. Am. Chem. Soc.* 2000, 122, 3112; Benites, et al., *J. Am. Chem. Soc.* 2000, 122, 7208.). The relative disposition of the alkyne termini and the nature of the ring closing are thought to provide steric contributions to the thermal barrier in the Bergman cyclization (Magnus, et al., *J. Am. Chem. Soc.* 1990, 112, 4986; Snyder, J. P., *J. Am. Chem. Soc.* 1990, 112, 5367).

The role of chelated transition metals in the Bergman cyclization of certain enediynes has been studied in some laboratories. Notably, the chelation of transition metals has been observed to reduce the thermal barrier in the Bergman cyclization of enediynes. However, heating to about 60° C. is still required for activation of such complexes, which is a relatively high temperature, and limits the usefulness of such compounds from a therapeutic standpoint. This problem can be avoided in some instances by using photoexcitation (e.g., photodynamic therapy ("PDT")), but such procedures are often limited in terms of therapeutic application, as a light source is required. In addition, long wavelength absorbing species are preferred in biological applications, which raises additional obstacles in terms of developing a therapeutic agent. Accordingly, there is a need for new enediyne ligands and metal complexes thereof, particularly such ligands and complexes that exhibit a lower energy barrier for undergoing the Bergman cyclization, and methods of therapeutically using such ligands and complexes.

The invention provides such tetradentate enediyne ligands and metal complexes thereof, and methods of using them in the treatment of cancer and infectious diseases. These and other advantages of the invention, as well as additional inventive features, will be apparent from the description of the invention provided herein.

BRIEF SUMMARY OF THE INVENTION

In one aspect, the invention provides novel tetradentate enediyne ligands that are thermally stable, yet react under photothermal conditions or thermally at about room temperature or slightly higher when complexed with one or more metal ions.

In another aspect, the invention provides a method of prophylactically or therapeutically treating cancer in a mammal (e.g., a human) comprising administering a therapeutically effective amount of a compound of the invention. The compound can be administered alone or as a composition that includes a therapeutically acceptable carrier. In accordance with the invention, the free uncomplexed ligand can be administered to the mammal, such that the ligand contacts a metal in vivo and forms a metal complex in vivo. Alternatively, a metal complex of the invention can be administered to the mammal so as to prophylactically or therapeutically treat cancer and/or an infectious disease in accordance with the invention.

The method of the present invention also includes administering a metal-complexed ligand to a mammal such that the complex contacts and exchanges with a metal in vivo which, in turn, forms a new metal complex in vivo.

BRIEF DESCRIPTION OF THE DRAWINGS

FIG. 6 illustrates a spectral analysis of a reaction mixture of an enediyne metal complex undergoing a Bergman cyclization.

DETAILED DESCRIPTION OF THE INVENTION

Figure 1:
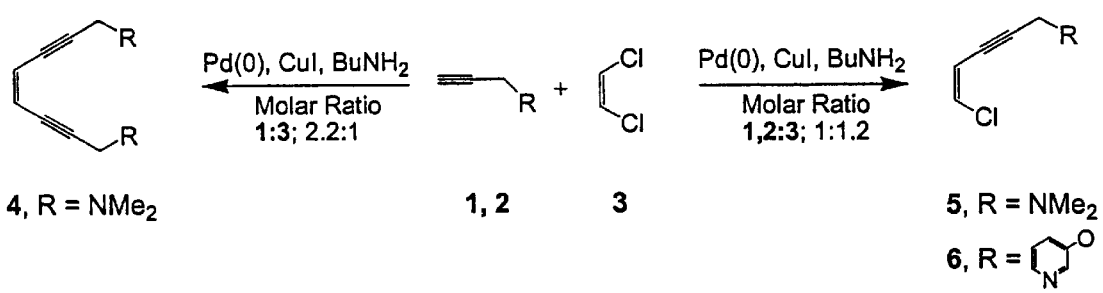
FIG. 1 illustrates the synthesis of a symmetric enediyne as well as the synthesis of an intermediate that can be used to prepare enediynes.

The present invention provides compound of the formula:

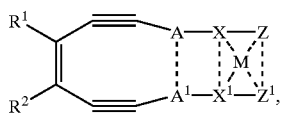

(I), wherein A and $A^1$ are the same or different and each is $(CR^3R^4)_m$, wherein m is an integer from 0 to 6, and $R^3$ and $R^4$ are the same or different and each is hydrogen, a halo, nitro, cyano, azido, or an organic group selected from the group consisting of linear $C_{1-12}$ alkyl, branched $C_{3-12}$ alkyl, $C_{2-12}$ alkenyl, $C_{3-30}$ cycloalkyl, $C_{3-30}$ heterocycloalkyl, $C_{6-30}$ aryl, $C_{5-30}$ heteroaryl, benzylcarbonyl, phenylcarbonyl, and a solubilizing group, wherein the organic group is unsubstituted or substituted with one or more substituents selected from the group consisting of a halo, nitro, cyano, azido, $C_{1-12}$ alkyl, $C_{6-30}$ aryl, or a solubilizing group; wherein the dotted line between A and $A^1$ represents an optional covalent bond linking A and $A^1$ together. X and $X^1$ are the same or different and each is a substituent comprising a nitrogen-, oxygen-, sulfur-, or phosphorus-containing functional group capable of forming a complex with a metal, wherein the dotted line between X and $X^1$ represents an optional covalent bond linking X and $X^1$ together. Z and $Z^1$ are the same or different and each is a substituent comprising a nitrogen-, oxygen-, sulfur-, or phosphorus-containing functional group capable of forming a complex with a metal, wherein the dotted line between Z and $Z^1$ represents an optional covalent bond linking Z and $Z^1$ together. $R^1$ and $R^2$ are the same or different and each is hydrogen, linear $C_{1-12}$ alkyl, branched $C_{3-12}$ alkyl, an aralkyl, $C_{3-30}$ aryl, a halo, nitro, or cyano. Alternatively, $R^1$ and $R^2$, together with the carbons to which they are bonded, can comprise $C_{6-30}$ aryl, $C_{3-30}$ heterocycle, or a macrocycle, wherein $R^1$ and $R^2$ are unsubstituted or substituted. Preferably, $R^1$ and $R^2$, together with the carbons to which they are bonded, form a benzene ring, that is optionally substituted. Substituents X, $X^1$, Z, and $Z^1$ preferably are capable of forming a tetradentate complex with a metal.

In a preferred embodiment, the compound of formula (I) further comprises a metal, which is preferably complexed with one or more functional groups on one or more substituents X, $X^1$, Z, or $Z^1$. In a particularly preferred embodiment, the metal forms a tetradentate complex with substituents X, $X^1$, Z, and $Z^1$. An exemplary tetradentate metal complex of the invention includes a tetradentate complex of the formula:

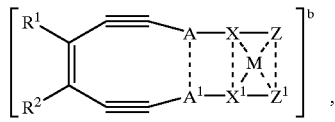

(II)

wherein M is a metal, b represents the charge of the complex and is an integer ranging from −3 to +3, and A, $A^1$, X, $X^1$, Z, $Z^1$, $R^1$, and $R^2$ are as described herein. The metal M can include any metal that is capable of forming a tetradentate complex with the compound of formula (I) in order to form a compound of formula (II). Suitable metals include, for example, Mg, Ca, Sr, Ba, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Ga, Sn, Pb, Ce, Eu, Gd, Tb, Dy, and Lu. Preferably, M is selected from the group consisting of Mg, Ca, Gd, Zn, and Cu.

Substituents X and $X^1$ include any suitable substituent that includes a heteroatom-containing functional group that is capable of forming a metal complex.

Suitable heteroatoms include, for example, N, O, S, P, and the like. Preferably, at least one of X or $X^1$ includes one or more functional groups selected from the group consisting of:

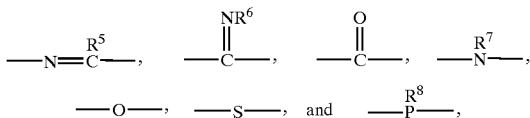

wherein $R^5$, $R^6$ and $R^8$ are each selected from the group consisting of hydrogen, $C_{1-12}$ alkyl, $C_{3-30}$ cycloalkyl, and $C_{6-30}$ aryl.

When A or $A^1$ is $(CR^3R^4)_m$, wherein m is from 0 to 6, it is at least one of $R^3$ and $R^4$ is an organic group selected from the group consisting of linear $C_{1-12}$ alkyl, branched $C_{3-12}$ alkyl, $C_{2-12}$ alkenyl, $C_{3-30}$ cycloalkyl, $C_{3-30}$ heterocycloalkyl, $C_{6-30}$ aryl, $C_{5-30}$ heteroaryl, benzylcarbonyl, phenylcarbonyl, and a solubilizing group, wherein the alkyl, alkenyl, cycloalkyl, heterocycloalkyl, heteroaryl, benzylcarbonyl, or phenylcarbonyl is unsubstituted or substituted with one or more substituents selected from the group consisting of a halo, nitro, cyano, azido, $C_{1-12}$ alkyl, or $C_{6-30}$ aryl. In a preferred embodiment, at least one of $R^3$ and $R^4$ is an organic group selected from the group consisting of $C_{1-12}$ alkyl or $C_{6-30}$ aryl, wherein the alkyl or aryl is unsubstituted or substituted with a halo, nitro, cyano, azido, $C_{1-12}$ alkyl, $C_{6-30}$ aryl, or a solubilizing group.

The term "solubilizing group" as used herein denotes any group that enables the compound to be soluble in a desired solvent, such as, for example, water or water-containing solvent. Furthermore, the solubilizing group can be one that increases the compound or complex's lipophilicity. Typically, the solubilizing group is, for example, hydroxyl, an amino, an ammonium salt, a phosphate, a sulfate, a carboxylic acid, or a carboxylic acid salt.

Substituents Z and $Z^1$ include any suitable substituent that includes a heteroatom-containing functional group that is capable of forming a metal complex. Suitable heteroatoms include, for example, N, O, S, P, and the like. Preferably, at least one of Z or $Z^1$ includes one or more functional groups selected from the group consisting of hydroxy, $C_{1-12}$ alkoxy, thio, $C_{1-12}$ alkylthio, $C_{6-30}$ arylthio, amino, $C_{1-12}$ alkylamino, $C_{1-12}$ dialkylamino, aryloxy (e.g., phenoxy), anilinyl, $C_{6-30}$ diarylphosphinyl, $C_{1-12}$ dialkylphosphinyl, (alkyl)arylphosphinyl, pyridinyl, pyrrolyl, pyrrolidinyl, piperdinyl, morpholinyl, imidazolyl, oxazolyl, benzofuranyl, benzoxazolyl, indolyl, thiofuranyl, furanyl, thiazolyl, quinolinyl, isoquinolinyl, pyrazinyl, and quinoxalinyl, wherein Z or $Z^1$ is unsubstituted or substituted with 1 to 3 substituents selected from the group consisting of $C_{1-12}$ alkyl, $C_{1-12}$ alkoxy, $C_{6-30}$ aryl, nitro, cyano, halo, amino, $C_{1-12}$ alkylarnino, and $C_{1-12}$ dialkylamino.

When Z or $Z^1$ includes a nitrogen-containing functional group, Z or $Z^1$ is preferably selected from the group consisting of:

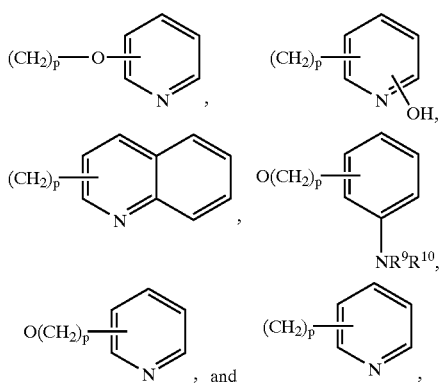

wherein p is an integer from zero to two, wherein $R^9$ and $R^{10}$ are each selected from the group consisting of hydrogen, $C_{1-12}$ alkyl, $C_{3-30}$ cycloalkyl, and $C_{6-30}$ aryl.

When Z or $Z^1$ includes an oxygen-containing functional group, Z or $Z^1$ is preferably selected from the group consisting of:

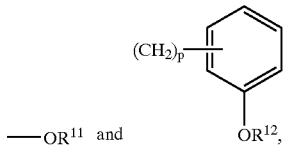

wherein p is an integer from zero to two, wherein $R^{11}$ and $R^{12}$ are each selected from the group consisting of hydrogen, $C_{1-12}$ alkyl, $C_{3-30}$ cycloalkyl, and $C_{6-30}$ aryl.

When Z or $Z^1$ includes a sulfur-containing functional group, Z or $Z^1$ is preferably selected from the group consisting of:

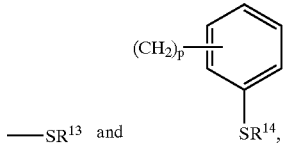

wherein p is an integer from zero to two, wherein $R^{13}$ and $R^{14}$ are each selected from the group consisting of hydrogen, $C_{1-12}$ alkyl, $C_{3-30}$ cycloalkyl, and $C_{6-30}$ aryl.

When Z or $Z^1$ includes a phosphorus-containing functional group, Z or $Z^1$ preferably is a diarylphosphine, which is more preferably a diphenylphosphine, which is unsubstituted or substituted on the phenyl rings.

An exemplary compound of formula (I) includes compound 14 (see, e.g., FIG. 4), which has the following structure:

(14)

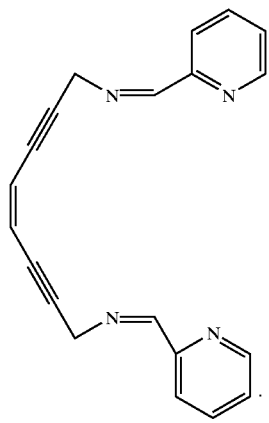

An exemplary compound of formula (II) includes the tetradentate metal complex of compound 14, which has the following structure:

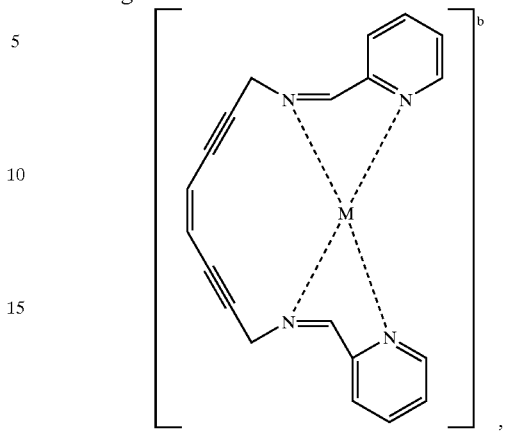

wherein M is selected from the group consisting of Mg, Ca, Sr, Ba, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Ga, Sn, Pb, Ce, Eu, Gd, Tb, Dy, and Lu, b represents the charge of the complex, and b is an integer ranging from −3 to +3. In a preferred embodiment, the tetradentate metal complex of compound 14 has a charge of +2 (i.e., b is +2), wherein M is selected from the group consisting of Mg, Zn, and Cu. An example of such a complex is shown, for example, in FIG. 4 (see compound 16).

Additional exemplary compounds of formula (I) include enediynes selected from the group consisting of:

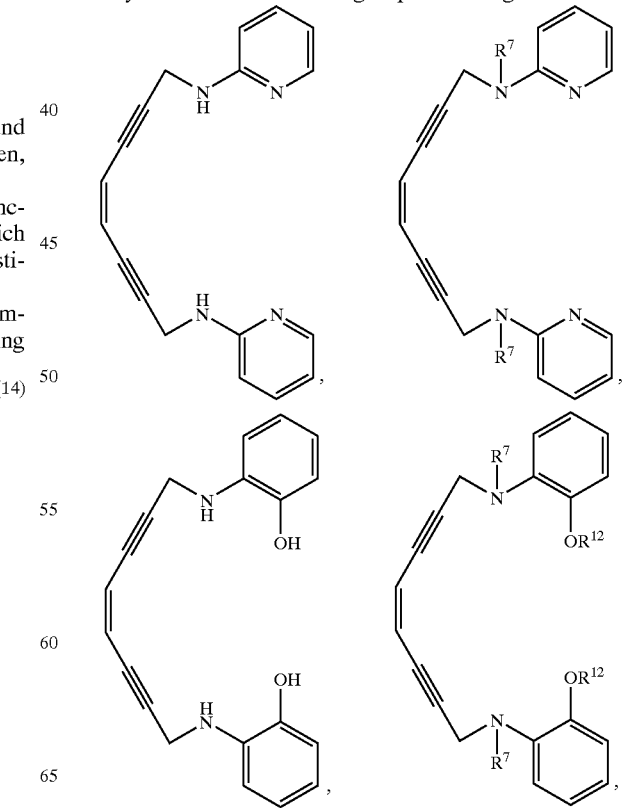

-continued

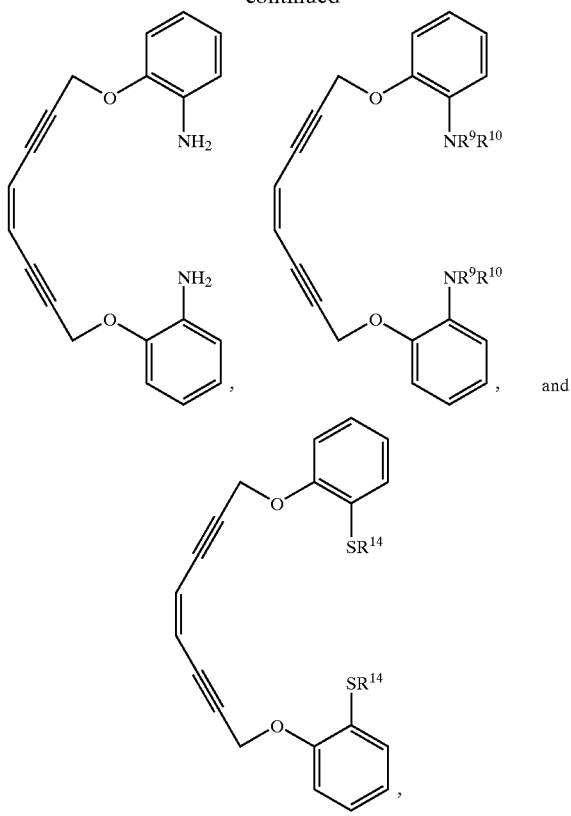

wherein $R^7$, $R^9$, $R^{10}$, $R^{12}$ and $R^{14}$ are each selected from the group consisting of hydrogen, $C_{1-12}$ alkyl, $C_{3-30}$ cycloalkyl, and $C_{6-30}$ aryl.

Substituents $R^1$ and $R^2$ include any suitable substituents and desirably include substituents that promote the enediyne cyclization reaction. Preferably, the substituents $R^1$ and $R^2$ are the same or different and each are selected from the group consisting of hydrogen, linear $C_{1-12}$ alkyl, branched $C_{3-12}$ alkyl, $C_{6-30}$ aryl, and an aralkyl. Alternatively, $R^1$ and $R^2$, together with the carbons to which they are bonded, can comprise $C_{6-30}$ aryl, $C_{3-30}$ heterocycle, or a macrocycle, wherein $R^1$ and $R^2$ are unsubstituted or substituted. Preferably, $R^1$ and $R^2$, together with the carbons to which they are bonded, form a benzene ring, that is optionally substituted. When $R^1$ or $R^2$ is substituted, it is preferably substituted with a substituent selected from the group consisting of a halo, hydroxy, $C_{1-12}$ alkyl, $C_{6-30}$ aryl, alkoxy, nitro, and cyano. In a particularly preferred embodiment, $R^1$ and $R^2$ are hydrogen.

The present invention includes compounds of formula (II) in which the metal, M, is complexed with at least one additional ligand that is capable of complexing with M. The additional ligand is preferably a ligand other than a ligand of the formula (I). When at least one additional ligand is complexed, the ligand can include, for example, a halogen-, nitrogen-, oxygen-, sulfur-, or phosphorus-containing functional group. Preferably, the additional ligand is selected from the group consisting of halo, hydroxy, $C_{1-12}$ alkoxy, thio, $C_{1-12}$ alkylthio, $C_{6-30}$ arylthio, cyano, nitro, amino, $C_{1-12}$ alkylamino, $C_{1-12}$ dialkylamino, phenoxy, anilinyl, $C_{6-30}$ diarylphosphinyl, $C_{1-12}$ dialkylphosphinyl, (alkyl) arylphosphinyl, pyridinyl, pyrrolyl, pyrrolidinyl, piperdinyl, morpholinyl, imidazolyl, oxazolyl, benzofuranyl, benzoxazolyl, indolyl, thiofuranyl, furanyl, thiazolyl, quinolinyl, isoquinolinyl, pyrazinyl, and quinoxalinyl. In addition, solvent molecules, such as, for example, THF, water or diethyl ether, etc., can serve as additional ligands.

Preferably, the compounds and metal complexes of the present invention undergo enediyne cyclization to form a benzenoid diradical at about room temperature (e.g., about 25° C.) or higher. More preferably, the compounds and metal complexes of the invention undergo enediyne cyclization at physiological temperatures, such as human physiological temperature, which is normally about 37° C. (about 98.6° F.). Compounds and metal complexes of the present invention can undergo enediyne cyclization without the use of light, avoiding the necessity of using photodynamic therapy. Alternatively, in some embodiments, the compounds of the invention can be reacted in the presence of light as in photodynamic therapy. In addition, some compounds and metal complexes of the present invention undergo enediyne cyclization under photothermal conditions and can be used photothermally in accordance with the therapeutic and prophylactic methods described herein.

As used herein, the term "photothermal" implies photo-induced Bergman cyclization through a thermal route involving non-radiative excited state decay rather than the established electronic excitation pathways (see, e.g., Evenzahav, et al., *J. Am. Chem. Soc.* 1998, 120, 1835–1841; Kaneko, et al., *Angew. Chem., Int. Ed. Engl.* 1999, 38, 1267–1268). Enediyne ligands of the present invention can be excited at any wavelength wherein Bergman cyclization is induced. Preferably the enediyne compound is excited in the infrared (IR) or near infrared (NIR) spectral region. The compounds can be excited by any means such as, for example, an Nd:YAG laser or diode laser. In a specific non-limiting example, an enediyne ligand-metal complex of the present invention is excited with either 1064 nm of a Nd:YAG laser (10 Hz, 1 mJ/pulse) or a 785 nm diode laser (2 mW, 60 s) in order to induce Bergman cyclization.

The invention further provides compositions, including pharmaceutical compositions, comprising a therapeutically effective amount of one or more of the compounds of the present invention, or a combination thereof, and a pharmaceutically acceptable carrier. Pharmaceutically acceptable carriers are also well known to those who are skilled in the art. The choice of carrier will be determined, in part, both by the particular composition and by the particular method used to administer the composition. Accordingly, there are a wide variety of suitable formulations of the pharmaceutical compositions of the present invention. Preferably the pharmaceutical composition comprises an anticancer effective or anti-infective effective amount of one or more compounds of the present invention.

The present invention includes a method of prophylactically or therapeutically treating cancer in a mammal (e.g., a human) comprising administering to a mammal in need thereof an anticancer effective amount (such as an antitumor effective amount) of a compound of formula (I), alone or in combination with a suitable carrier. Preferably, when the compound of formula (I) is administered in accordance with the present inventive method, it forms a tetradentate metal complex with a metal found in vivo. The complex thereby formed preferably is capable of forming a benzenoid diradical under physiological conditions and/or under photothermal conditions.

The present invention also includes a method of prophylactically or therapeutically treating cancer in a mammal (e.g., a human) comprising administering to a mammal in need thereof an anticancer effective amount (such as an antitumor effective amount) of an enediyne tetradentate metal complex of formula (II), alone or in combination with a suitable carrier. Preferably, when the complex of formula (II) is administered in accordance with the present invention, it is capable of forming a benzenoid diradical under physiological conditions and/or under photothermal conditions.

The invention relates to a method of prophylactically or therapeutically treating an infection by a microorganism in a mammal (e.g., a human) comprising administering to a mammal in need thereof an anti-infective effective amount of an enediyne tetradentate metal complex or composition of formula (II), alone or in combination with a suitable carrier. Preferably, when the complex is administered in accordance with the invention, it is capable of forming a benzenoid diradical under physiological conditions and/or under photothermal conditions.

The invention also relates to a method of prophylactically or therapeutically treating a virus in a mammal (e.g., a human) comprising administering to a mammal in need thereof a an antiviral effective amount of an enediyne tetradentate metal complex or composition of formula (II), alone or in combination with a suitable carrier. Preferably, when the complex is administered in accordance with the present invention, it is capable of forming a benzenoid diradical under physiological conditions and/or under photothermal conditions.

The therapeutic and prophylactic methods of the present invention include administering a compound of formula (II), alone or in combination with a suitable carrier, wherein the metal M exchanges with a different metal in vivo to form a second tetradentate metal complex in vivo. The metal complex thus administered preferably does not undergo enediyne cyclization under physiological conditions. It is preferred that the second tetradentate metal complex (formed in vivo) is capable of forming a benzenoid diradical under physiological conditions and/or under photothermal conditions.

In accordance with the therapeutic and prophylactic methods of the present invention, one or more compounds or compositions of the invention can be administered by any suitable route, for example, orally, intramuscularly, subcutaneously, intravenously, or the like. The composition can be present as a solution suitable, for example, for intravenous injection or infusion.

One skilled in the art will appreciate that suitable methods of administering a diazeniumdiolate composition of the present invention to an animal, e.g., a mammal such as a human, are known, and, although more than one route can be used to administer a particular composition, a particular route can provide a more immediate and more effective reaction than another route. Formulations suitable for oral administration can consist of (a) liquid solutions, such as an effective amount of the diazeniumdiolate dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Compounds and compositions of formula (I) and/or (II) of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The composition also can be present in unit dosage form, such as, for example, a tablet or capsule. The therapeutically effective amount is the dose necessary to achieve an "effective level" of the active compound in the individual patient. The therapeutically effective amount can be defined, for example, as that amount required to be administered to an individual patient to achieve an anticancer effective level of a compound of the present invention to kill or inhibit the growth of the cancer; the effective level might be chosen, for example, as that level to kill or inhibit the growth of tumor cells in a screening assay. Since the "effective level" is used as the preferred endpoint for dosing, the actual dose and schedule can vary, depending upon interindividual differences in pharmacokinetics, drug distribution, and metabolism. The "effective level" can be defined, for example, as the level desired in the patient that corresponds to a concentration of a compound of the present invention which kills or inhibits the growth of human cancers in an assay which can predict for clinical anticancer activity of chemical compounds. The "effective level" for compounds of the present invention can vary when these compounds are used in combination with other anticancer compounds or combinations thereof.

Alternatively, the "effective level" can be defined, for example, as that concentration of the compound of the present invention needed to inhibit markers of the cancer in the patient's blood, or which slows or stops the growth of the patient's cancer, or which causes the patient's cancer to regress or disappear, or which renders the patient asymptomatic to the particular cancer, or which renders an improvement in the patient's subjective sense of condition. Since a fixed "anticancer effective amount" is used as the preferred endpoint for dosing, the actual dose and schedule for drug administration for each patient can vary depending upon interindividual differences in pharmacokinetics, drug disposition, and metabolism. Moreover, the dose can vary when the compound is used in combination with other drugs.

One skilled in the art can easily determine the appropriate dose, schedule, and method of administration for the exact formulation of the composition being used, in order to achieve the desired effective level in the individual patient. One skilled in the art also can readily determine and use an appropriate indicator of the effective level of the compounds of the present invention by a direct (e.g., analytical chemistry) and/or indirect (e.g., with clinical chemistry indicators) analysis of appropriate patient samples (e.g., blood and/or tissues), or by direct or indirect observations of the shrinkage or inhibition of growth of the individual patient's tumor. There are many references in the art that teach how one works out the protocols of administering anticancer agents to patients (see, e.g., "Cancer Chemotherapy: Principles and Practice" ed., Chabner and Collins, J. B. Lippincott, 1990, especially chapter 2, by J. B. Collins).

In some embodiments, the present method of treating cancer using the compounds and compositions of the present invention can be made more effective by administering other anticancer compounds along with the compound of the present invention. These other anticancer compounds include, but are not limited to, all of the known anticancer compounds approved for marketing in the United States and those that will become approved in the future. See, for example, Table 1 and Table 2 of Boyd "The Future of Drug Development", *Current Therapy in Oncology*, Section I. Introduction to Cancer Therapy (J. E. Niederhuber, ed.), Chapter 2, by B.C. Decker, Inc., Philadelphia, 1993, pp. 11–22. More particularly, these other anticancer compounds include doxorubicin, bleomycin, vincristine, vinblastine, VP-16, VW-26, cisplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

When the therapeutic or prophylactic method of the present invention is utilized in the treatment of infections by viruses and microorganisms in a host, e.g., a mammal, such as a human, it will be appreciated that the specifications for the unit dosage forms of the present invention may depend on the particular compound or compounds employed and the effect to be achieved, as well as the pharmacodynamics associated with each compound in the host. The dose administered should be a "therapeutically effective amount" or an amount necessary to achieve an "effective level" in the individual patient.

Since the "effective level" is used as the preferred endpoint for dosing, the actual dose and schedule may vary, depending upon interindividual differences in pharmacokinetics, drug distribution, and metabolism. The "effective level" may be defined, for example, as the blood or tissue level desired in the patient that corresponds to a concentration of one or more compounds of the invention which inhibits a microorganism or virus in an assay known to predict for clinical antiviral activity of chemical compounds. The "effective level" for compounds which are the subject of the present invention also may vary when the compositions of the present invention are used in combination other known anti-infective compounds or combinations thereof.

One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with surrogate indicators) analysis of appropriate patient samples (e.g., blood and/or tissues).

In the treatment of some infected (e.g., virally) individuals, it may be desirable to utilize a "mega-dosing" regimen, wherein a large dose is administered, time is allowed for the compound to act, and then a suitable reagent is administered to the individual to inactivate the compound.

The pharmaceutical composition may contain other pharmaceuticals, in conjunction with the compounds of the invention. Representative examples of these additional pharmaceuticals include antiviral compounds, immunomodulators, immunostimulants, and antibiotics. Exemplary antiviral compounds include 3'-azido-2',3'-dideoxythymidine (AZT), 2'3'-dideoxyinosine (ddI), 2'3'-dideoxycytidine (ddC), 2'3'-didehydro-2',3'-dideoxythymidine (D4T), 9-(1,3-dihydroxy-2-propoxymethyl)guanine (gancyclovir), fluorinated dideoxynucleotides such as 3'-fluoro-2',3-dideoxythymidine, nonnucleoside compounds such as 6,11-dihydro-11-cyclopropyl-4-methyldipyrido[2,3-b:2',3'-e]-[1,4]diazepin-6-one (nevirapine) (Shih et al., *PNAS*, 88, 9878–9882 (1991)), TIBO and analogs and derivatives such as (+)-S,4,5,6,7-tetrahydro-9-chloro-5-methyl-6-(3-methyl-2-butenyl)-imidazo[4,5,1-jk][1,4]-benzodiazepin-2(1H)-thione (R82913) (White et al., *Antiviral Research*, 16, 257–266 (1991)), Ro 31-8959 (Craig et al., *Antiviral Research*, 16, 295–305 (1991)), BI-RJ-70 (Shih et al., supra), 9-(2-hydroxyethoxy-methyl)guanine (acyclovir), α-interferon, recombinant CD4 (Merigan et al., *The American Journal of Medicine*, 90 (Suppl. 4A), 8S–17S (1991)), pyridine analogs such as (3-[(benzoxazol-2-yl)ethyl]-5-ethyl-6-methylpyridin-2(1H)-one (L-696,229), 1-[(2-hydroxyethoxy)methyl]-6-phenylthiothymine (HEPT), carbocyclic 2',3'-didehydro-2',3'-dideoxyguanosine (carbovir), and [2',5'-Bis-O-(tert-butyldimethylsilyl)-β-D-ribofuranosyl]-3'-spiro-5"-(4"-amino-1",2"-oxathiole-2",2"-dioxide)thymine (TSAO-T). Exemplary immunomodulators and immunostimulants include various interleukins, CD4, cytokines, antibody preparations, blood transfusions, and cell transfusions. Exemplary antibiotics include antifungal agents, antibacterial agents, and anti-*Pneumocystis carnii* agents.

The term "alkyl," as used herein, means a linear or branched alkyl substituent containing from, for example, about 1 to about 12 carbon atoms, preferably from about 1 to about 8 carbon atoms, more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like. The alkyl group is preferably an alkyl group that promotes or enhances therapeutically desirable properties with respect to the compounds of the present invention, for example, anti-cancer or anti-microbial activity, metabolic stability, bioavailability, tissue distribution, improved pharmacokinetic properties, and the like, as will be appreciated by one of ordinary skill in the art.

The term "alkenyl," as used herein, means a linear or branched alkenyl substituent containing from, for example, about 2 to about 12 carbon atoms, preferably from about 2 to about 8 carbon atoms, more preferably from about 3 to about 6 carbon atoms. Examples of such substituents include propenyl, isopropenyl, n-butenyl, sec-butenyl, isobutenyl, tert-butenyl, pentenyl, isopentenyl, hexenyl, octenyl, dodecenyl, and the like.

The term "halo" or "halogen," as used herein, means a substituent selected from Group VIIA, such as, for example, fluorine, bromine, chlorine, and iodine. Preferably, the halo is bromine or chlorine.

The term "aryl" refers to an unsubstituted or substituted aromatic carbocyclic substituent, as commonly understood in the art, and includes monocyclic and polycyclic aromatics such as, for example, phenyl, biphenyl, naphthyl substituents, and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms.

The term "cycloalkyl," as used herein, means a cyclic alkyl substituent containing from, for example, about 3 to about 30 carbon atoms, preferably from about 5 to about 14 carbon atoms, more preferably from about 5 to about 6 carbon atoms. Examples of such substituents include cyclopropyl, cyclobutyl, cyclopentyl, cyclohexyl, and the like.

The term "alkoxy" embraces linear or branched alkyl groups that are attached to divalent oxygen. The alkyl group is the same as described herein. Examples of such substituents include methoxy, ethoxy, t-butoxy, and the like. The aryl group is the same as described herein. The term "aryloxy" refers to substituents that have an aryl group attached to divalent oxygen. Examples of such substituents include phenoxy.

The terms "alkylthio" and "arylthio" as used herein, denote a substituent with either an alkyl or aryl group directly attached to a divalent sulfur atom. The alkyl or aryl group is the same as described herein. Examples of such substituents include methylthio, ethylthio, phenylthio, and the like.

The terms "dialkylphosphinyl" and "diarylphosphinyl" as used herein refer to a trivalent phosphorus atom connected to two alkyl groups and two aryl groups, respectively, directly attached thereto. Examples of such substituents include dibutylphosphinyl and diphenylphosphinyl and the like. The term "(alkyl)arylphosphinyl" as used herein refers to a trivalent phosphorus atom with an alkyl group and an aryl group directly attached thereto. Examples of such substituents include (propyl)phenylphosphinyl and the like. The alkyl and aryl groups are the same as described herein.

The term "alkylamino" refers to a secondary amine substituent with oone hydrogen and one alkyl group directly attached to a trivalent nitrogen atom. The term "dialkyl amino" refers to a tertiary amine substituent with two of the same or different alkyl groups directly attached to a trivalent nitrogen atom. The alkyl group is the same as described herein.

The term "trialkylsilyl" as utilized herein means three alkyl groups (the same or different) as defined herein, directly attached to a tetravalent silicon atom. Examples of such substituents include, for example, trimethylsilyl, methyl(dibutyl)silyl, tri-iso-propylsilyl, and the like.

The term "aralkyl" as utilized herein means alkyl as defined herein, wherein at least one hydrogen atom is replaced with an aryl substituent as defined herein. Aralkyls include, for example, benzyl, phenethyl, or substituents of the formula:

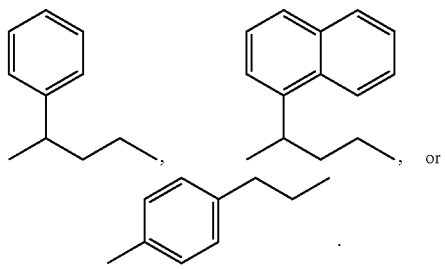

The term "heterocycloalkyl" means a cycloalkyl substituent as defined herein (including polycyclics), wherein at least one carbon which defines the carbocyclic skeleton is substituted with a heteroatom such as, for example, O, N, or S, optionally comprising one or more double bond within the ring, provided the ring is not heteroaryl as defined herein. The heterocycloalkyl preferably has 3 to about 30 atoms (members) in the carbocyclic skeleton of each ring, preferably about 4 to about 7 atoms, more preferably 5 to 6 atoms. Examples of heterocycloalkyl substituents include epoxy, aziridyl, oxetanyl, tetrahydrofuranyl, dihydrofuranyl, piperadyl, piperidinyl, pyperazyl, piperazinyl, pyranyl, morpholinyl, and the like.

The term "heteroaryl" means a substituent defined by an aromatic heterocyclic ring, as is commonly understood in the art, including monocyclic and polyclic heteroaryls containing from, for example, about 3 to about 30 carbon atoms, preferably from about 5 to about 10 carbon atoms, more preferably from about 5 to about 6 carbon atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

It will also be appreciated that some polycyclic heterocyclic rings contain an aromatic ring and a non-aromatic ring. Examples of such polycyclic substituents include, for example, benzotetrahydrofuranyl, benzopyrrolidinyl, benzotetrahydrothiophenyl, and the like.

The following examples further illustrate the invention but should not be construed as in any way limiting its scope.

All preparations were carried out in an inert atmosphere (nitrogen) using Schlenk and drybox techniques. Chemicals used in the syntheses were of the highest purity available from Aldrich Chemical Company and used as received. Dichloromethane was dried and distilled from calcium hydride. The organic compounds were purified by flash chromatography with 60 Å Silica gel (430–230 μm) using HPLC grade solvents. $^1$H and $^{13}$C NMR were recorded on VXR 400 MHz NMR spectrometer using the residual proton resonance as an internal reference. The multiplicity of the $^{13}$C signals was determined by the DEPT technique. EI and FAB MS spectra were acquired on a Kratos MS-80 mass spectrometer that was interfaced with a Kratos DS90 data system. Differential scanning calorimetry traces were recorded on a General V4.1C DuPont 910 DSC differential scanning calorimeter coupled to a Dupont Thermal Analyst 2100 at a heating rate of 10° C. min$^{-1}$.

EXAMPLE 1

This example illustrates the synthesis of the symmetric dimethylamino enediyne (1,8-bis(dimethylamino)oct-4-ene-2,6-diyne, 4), as well as the dimethylamnino (5) and 3-hydroxypyridine (6) substituted 5-chloro-ene-2-yne synthon.

Stephens-Castro coupling of 2.2 equiv of the dimethylamino alkyne (1) with cis-1,2-dichloroethylene (3) over a Pd(0) catalyst in the presence of Cu(I) and BuNH$_2$ generated 4 in 79% yield, as depicted in FIG. 1. Comparable reaction conditions with 1:1.2 alkyne 1, 2:3 stoichiometries produced the monosubstituted eneyne precursors 5, 6 in 55–65% yield.

Symmetric enediyne (4) was prepared by adding alkyne (2.2 mol) in a mixture of cis-1,2-dichloroethylene (3) (1 mol), Pd(PPh$_3$)$_4$ (0.06 mol), CuI (0.2 mol), n-butylamine (5 mol) in benzene at 45° C. and stirring the mixture for 4 hours at that temperature (Chemin, et al., *Tetrahedron*, 50, 5335 (1994)). The crude product was purified by flash column chromatography (5% ethyl acetate:dichloromethane).

Spectral data for (4): Yield: 79%; $^1$H NMR (400 MHz, CDCl$_3$): 2.19 (s, 12H, CH$_3$), 3.33 (s, 4H, NCH$_2$), 5.71 (s, 2H, CH); $^{13}$C NMR (CDCl$_3$): 44.16 (NCH$_3$), 48.84 (NCH$_2$), 83.02 (Cquart), 93.34 (Cquart), 119.38 (CH); MS: m/z; 191.2 (M$^+$+1).

Spectral data for (5): Yield 62%; $^1$H NMR (400 MHz, CDCl$_3$): 2.32 (s, 6H, NCH$_3$), 3.44 (s, 2H, NCH$_2$), 5.88 (d, J=8 Hz, 1H, CH), 6.36 (d, J=8 Hz, 1H, CH); $^{13}$C NMR (CDCl$_3$): 44.39 (NCH$_3$), 48.93 (NCH$_2$), 79.50 (Cquart), 93.64 (Cquart), 112.24 (CH), 128.25 (CH); MS: m/z; 145 (M$^+$+2), 143 (M$^+$).

Spectral data for (6): Yield: 57%; $^1$H NMR (400 MHz, CDCl$_3$): 4.95 (s, 2H, OCH$_2$), 5.90 (d, J=8 Hz, 1H, CH), 6.46 (d, J=8 Hz, 1H, CH), 7.25–7.33 (m, 2H), 8.27 (m, 1H), 8.42 (s, 1H); $^{13}$C NMR (CDCl$_3$): 56.95 (OCH$_2$), 82.0 (Cquart), 91.23 (Cquart), 111.28 (CH), 121.94 (CH), 123.98 (CH), 130.97 (CH), 138.70 (CH), 143.05 (CH), 153.94 (Cquart); Mass: m/z; 195 (M$^+$+2), 193 (M$^+$), 158, 130.

EXAMPLE 2

This example illustrates the synthesis of asymmetric enediyne chelates of the form 1,8-bis(R,R')oct-4-ene-2,6-diyne where R and R'=dimethylamino, amino, N-Boc-protected amino, or 3-hydroxypyridine (7, 8, 9) from dimethylamino (5) and 3-hydroxypyridine (6) substituted 5-chloro-ene-2-yne.

Figure 2:
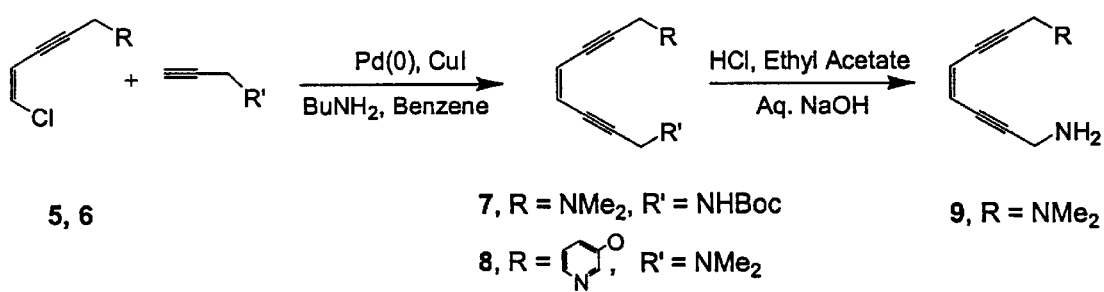
FIG. 2 illustrates the synthesis of an asymmetric enediyne.
Figure 3:
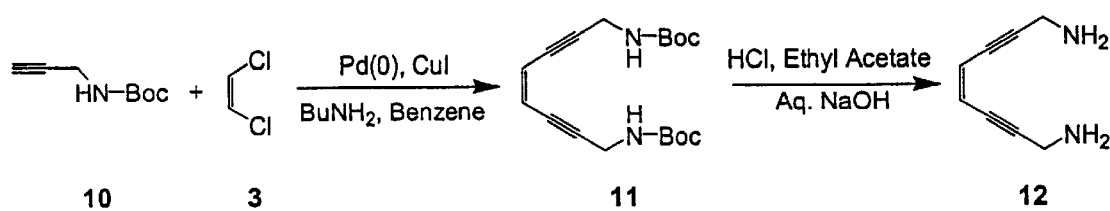
FIG. 3 illustrates the synthesis of 1,8-diaminooct-4-ene-2,6-diyne (12) from N-t-Boc-propargyl amine (10) and cis-dichloroethylene (3).

Reaction of 5 with 1 equiv of the N-Bocpropargyl amine (10), or 6 with 1 under analogous conditions yielded the asymmetric products 7, 8 as depicted in FIG. 2. Subsequent treatment of 7 with acid removed the protecting group and generated the asymmetric primary/tertiary amine species 9. The syntheses of 11 and 12 are directly analogous to that of 4 and 9. The same N-Bocpropargyl amine (10) was employed for the preparation of the N-Boc enediyne precursor 11 and the subsequent diamino product 12 by analogy as illustrated in FIG. 3. Deprotection of the Boc group was achieved by stirring (11) with 37% HCl in ethyl acetate and a workup with aqueous sodium hydroxide.

Spectral data for (7): Yield: 65%; $^1$H NMR (400 MHz, CDCl$_3$): 1.45 (s, 9H, CH$_3$), 2.35 (s, 6H, NCH$_3$), 3.46 (s, 2H, NCH$_2$), 4.12 (s, 2H, NCH$_2$), 5.09 (s, 1H, NH), 5.82 (m, 2H, CH); $^{13}$C NMR (CDCl$_3$): 28.66 (CH$_3$), 31.66 (NCH$_2$), 44.34 (NCH$_3$), 49.04 (NCH$_2$), 80.17 (Cquart), 81.03 (Cquart), 82.96 (Cquart), 93.09 (Cquart), 92.18 (Cquart), 119.18 (CH), 120.29 (CH), 155.59 (CO); MS: m/z; 262.16 (M$^+$).

Spectral data for (8): Yield: 62%; $^1$H NMR (400 MHz, CDCl$_3$): 2.28 (s, 6H, NCH$_3$), 3.39 (s, 2H, NCH$_2$), 4.90 (s, 2H, OCH$_2$), 5.78 (d, J=8 Hz, 1H, CH), 5.88 (d, J=8 Hz, 1H, CH), 7.20–7.27 (m, 1H), 7.28–7.31 (m, 1H), 8.25 (m, 1H), 8.38 (d, J=4 Hz, 1H); $^{13}$C NMR (CDCl$_3$): 44.25 (NCH$_3$), 48.87 (NCH$_2$), 57.12 (OCH$_2$), 82.65 (Cquart), 85.51 (Cquart), 90.19 (Cquart), 93.72 (Cquart), 118.14 (CH), 121.36 (CH), 121.89 (CH), 124.02 (CH), 138.66 (CH), 143.04 (CH), 154.13 (Cquart); MS: m/z; 239.1 (M$^+$–1), 196.1, 145.1.

Spectral data for (9): Yield: 72%; $^1$H NMR (400 MHz, CDCl$_3$): 1.42 (brs, 2H, NH$_2$), 2.34 (s, 6H, NCH$_3$), 3.47 (s, 4H, NCH$_2$), 3.67 (s, 2H, NCH$_2$), 5.81 (s, 2H, CH); $^{13}$C NMR (CDCl$_3$): 32.34 (NCH$_2$), 44.33 (NCH$_3$), 49.02 (NCH$_2$), 80.36 (Cquart), 83.04 (Cquart), 92.65 (Cquart), 119.43 (CH), 119.49 (CH); MS: m/z; 162.1 (M$^+$), 132.1.

Spectral data for (11): Yield: 68%; $^1$H NMR (400 MHz, CDCl$_3$): 1.44 (s, 18H, CH$_3$), 4.10 (s, 4H, NCH$_2$), 4.93 (brs, 2H, NH), 5.78 (s, 2H, CH); $^{13}$C NMR (CDCl$_3$): 28.67 (CH$_3$), 31.65 (NCH$_2$), 80.29 (Cquart), 80.55 (Cquart), 93.70 (Cquart), 119.91 (CH), 155.68 (CO); MS: FAB; 335 (M$^+$+1).

Spectral data for (12): Yield: 70%; $^1$H NMR (400 MHz, CDCl$_3$): 1.44 (s, 4H, NH$_2$), 3.54 (s, 4H, NCH$_2$), 5.72 (s, 2H, CH); $^{13}$C NMR (CDCl$_3$): 32.52 (NCH$_2$), 79.90 (Cquart), 98.21 (Cquart), 119.15 (CH); MS: m/z; 134.1 (M$^+$+1).

EXAMPLE 3

The example illustrates the synthesis of (Z)-N,N'-Bis[1-pyridin-2-yl-meth-(E)-ylidene]oct-4-ene-2,6-diyne-1,8-diamine or (PyimED, 14).

Figure 4:
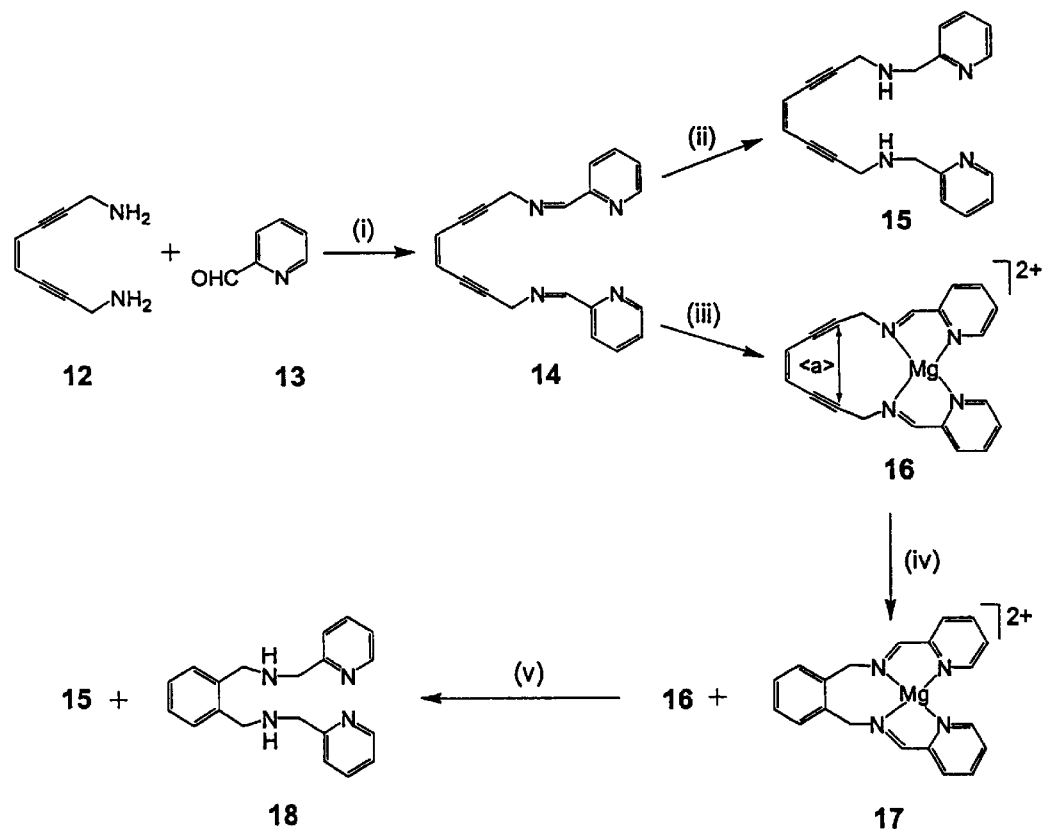
FIG. 4 illustrates the synthesis of an enediyne, a tetradentate metal complex thereof, and the Bergman cyclization of the metal complex.

1,8-Diaminooct-4-ene-2,6-diyne (12) (0.5 g, 3.7 mmol) in 10 mL dichloromethane was added to a stirring solution of pyridine-2-carboxaldehyde (13) (0.89 g, 7.4 mmol) in 30 mL dichloromethane containing molecular sieves as depicted in FIG. 4. The reaction mixture was stirred for 2.5 h at room temperature and then exposed to 5% charcoal for 30 min. The mixture was filtered through a celite bed, and the solvent was removed under vacuum. Cooling of the sample at 5° C. for 24 h yielded a solid compound that was subsequently washed with hexane and filtered.

Spectral data for (14): Yield: 75%; Mp: 60° C.; $^1$H NMR (400 MHz, CDCl$_3$): 4.86 (s, 4H, NCH$_2$), 5.97 (s, 2H, CH), 7.31 (t, 2H), 7.73 (t, 2H), 7.95 (d, 2H), 8.64 (d, 2H), 8.81 (s, 2H); $^{13}$C NMR (CDCl$_3$): 48.08 (NCH$_2$), 85.93 (Cquat), 91.99 (Cquat), 119.71 (CH), 121.64 (CH), 125.06 (CH), 136.71 (CH), 149.66 (CH), 154.57 (Cquat), 163.20 (CH); MS (FAB), m/z: 313 (M$^+$+H); HR-MS(EI), m/z: 312.13669 [M$^+$ calcd. for C$_{20}$H$_{16}$N$_4$: 312.13680]; IR (KBr, cm$^{-1}$): 3047,3004,2941,2903, 2217, 1649, 1587, 1567, 1467, 1438, 1352, 1313, 1154, 1090, 995, 772, 750, 618.

EXAMPLE 4

This example illustrates the synthesis of N,N-Bis-pyridin-2-ylmethyl-oct-4-ene-2,6-diyne-1,8-diamine (15).

Reduction of 14 with 2.5 equivalent of NaBH$_4$ produced the reduced enediyne 15 in 84% yield as depicted in FIG. 4. The crude enediyne was chromatographed (flash chromatography) on silica gel (10% Ethyl acetate/dichloromethane).

Spectral data for (15): $^1$H NMR (CDCl$_3$): 2.10 (brs, 2H, NH)), 3.69 (s, 4H NCH$_2$), 4.03 (s, 4H, NCH$_2$Py), 5.82 (s, 2H), 7.12–7.16 (m, 2H), 7.32 (d, 2H), 7.59–7.65 (m, 2H), 8.52 (d, 2H); $^{13}$C NMR (CDCl$_3$): 38.8 (NCH$_2$), 53.6 (NCH$_2$Py), 81.4 (Cquat 95.1 (Cquat), 119.2 (CH), 121.9 (CH), 122.3 (CH), 136.4 (CH), 149.3 (CH), 159.2 (Cquat); MS (FAB), m/z: 317 (M$^+$+H); HR-MS(EI), m/z: 316.17007 [M$^+$ calcd. for C$_{20}$H$_{20}$N$_4$: 316.1680]; IR (KBr, cm$^{-1}$): 3278, 3009,2912,2205, 1590, 1569, 1473, 1432, 1356, 1327, 1147, 1120, 1047, 994, 756.

EXAMPLE 5

This example illustrates the synthesis of [Mg(PyimED)]Cl$_2$ (16).

To a solution of 14 (100 mg) in methanol (20 mL), a solution of MgCl$_2$.6H$_2$O (64.8 mg) in 5 mL MeOH was added at 0° C., and the reaction mixture was stirred at that temperature for 8 h as depicted in FIG. 4. The solvent was removed at the same temperature; the product was washed with ether, air dried for 1 h, and stored at 5° C.

Spectral data for (16): $^1$H NMR (CD$_3$OD): 4.83 (s, 4H), 6.06 (s, 2H), 7.43 (t, 2H), 7.84 (t, 2H), 7.93 (d, 2H), 8.57 (d, 2H), 8.75 (s, 2H); $^{13}$C NMR (CD$_3$OD): 48.45 (NCH$_2$), 87.26 (Cquat), 92.43 (Cquat), 120.84 (CH), 122.88 (CH), 127.0 (CH), 138.85 (CH), 150.38 (CH), 154.89 (Cquat), 163.63 (CH). MS, m/z: 373, 371 ($^{35/37}$Cl-M$^+$), 336, 289, 167; HR-MS(EI), m/z: 373.1526, 371.1526 [M$^+$-Cl calcd. for C$_{20}$H$_{16}$ClN$_4$Mg: 373.11004/371.11004]; IR (KBr, cm$^{-1}$): 3010, 2914, 2182, 1598, 1570, 1473, 1437, 1323, 1224, 1155, 1104, 1052, 773, 640.

EXAMPLE 6

This example illustrates the synthesis of pyridin-2-ylmethyl-(2-{[(pyridin-2-ylmethylene)-amino]-methyl}-benzyl)-amine (20).

Figure 5:
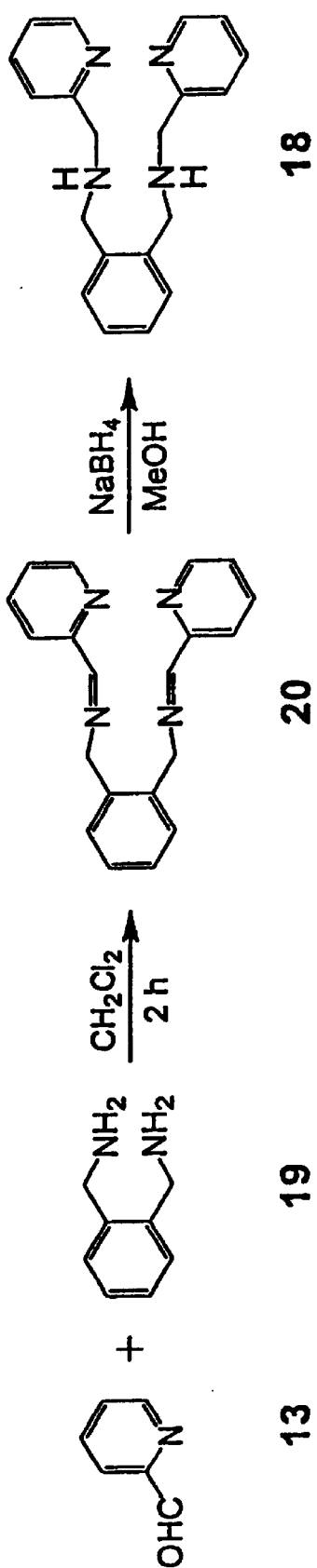
FIG. 5 illustrates the synthesis of a compound that is believed to be a product from the Bergman cyclization of an enediyne.

A solution of o-xylenediamine (19) (1 eq) in dichloromethane was added in a suspension of pyridine-2-carboxaldehyde (13) (2 eq) in dichloromethane containing molecular sieves as depicted in FIG. 5. The reaction mixture was stirred at room temperature for 2 h, and the solvent was removed under vacuum.

Spectral data for (20): $^1$H NMR (CD$_3$OD): 5.03 (s, 4H, NCH$_2$), 7.30–7.44 (m, 6H), 7.83 (t, 2H), 7.98 (d, 2H), 8.42 (s, 2H), 8.55 (d, 2H); $^1$H NMR (CDCl$_3$): 5.04 (s, 4H, NCH$_2$), 7.27–7.37 (m, 6H), 7.72 (t, 2H), 8.05 (d, 2H), 8.47 (s, 2H), 8.62 (d, 2H); $^{13}$C NMR (CDCl$_3$): 62.13 (NCH$_2$), 121.27 (CH), 124.72 (CH), 127.65 (CH), 129.26 (CH), 136.46 (CH), 136.87 (Cquat), 149.24 (CH), 154.46 (Cquat), 162.76 (CH); MS, m/z: 314 (M$^+$), 222, 208, 193, 130, 118, 93; HR-MS(EI), m/z: 314.15347 [M$^+$ calcd. for C$_{20}$H$_{18}$N$_4$: 314.15240].

EXAMPLE 7

This example illustrates the synthesis of pyridin-2-ylmethyl-(2-{[(pyridin-2-yl-methyl)-amino]-methyl}-benzyl)-amine (18).

Reduction of 20 with excess NaBH$_4$ produced compound 18 as depicted in FIG. 5.

Spectral data for (18): $^1$H NMR (CDCl$_3$): 2.10 (brs, 2H), 3.89 (s, 4H, NCH$_2$Ph), 3.95 (s, 4H, NCH$_2$Py), 7.14 (t, 2H), 7.23–7.35 (m, 6H), 7.56 (t, 2H), 8.52 (d, 2H); $^{13}$C NMR (CDCl$_3$): 51.65 (NCH$_2$Ph), 54.83 (NCH$_2$Py), 121.81 (CH), 122.23 (CH), 127.37 (CH), 130.20 (CH), 136.36 (CH), 138.69 (Cquat), 149.13 (CH), 159.89 (Cquat); MS, m/z: 319 (M$^+$+H), 210, 93; HR-MS(EI), m/z: 318.1831 [M$^+$ calcd. for C$_{20}$H$_{22}$N$_4$: 318.1836].

EXAMPLE 8

This example illustrates the Bergman enediyne cyclization temperatures of several compounds of the present invention and NMR data indicating enediyne cyclization occurring at ambient temperature.

The Bergman enediyne cyclization temperatures of enediynes 4, 8, 9, 12, and 14 (Table 1) were measured on neat materials by differential scanning calorimetry (DSC) and showed a remarkable 80° C. variation across the series. It is believed that the origin of the gradient derived from the steric encumbrance imposed upon the alkyne terimini by the nitrogen-containing substituents at the 1,8 positions of the enediyne framework. Begining with R=R'=dimethylamino, 4 was a thermally stable compound that exhibited a Bergman cyclization temperature of 186° C. Substitution of one dimethylamino group with 3-hydroxypyridine (8) dramatically reduced the Bergman cyclization temperature to 149° C. It is believed that this result derived primarily from two sources: the ability of the pyridine ring to rotate out of the enediyne plane about the oxygen bond relieved steric clashes with the opposing substituent; the addition of the step sp$^3$ oxygen between the pyridine ring and the alkyne termini effectively distanced the substituent from the alkyne termini by another atom, further reducing the interaction between substituents. This latter effect played an important role as subsequent substitution to form the 1,8-bis(pyridine-3-oxy)oct-4-ene-2,6-diyne (bpod) compound restored the adjacent proximity of the substituents and resulted in only a modest decrease of the Bergman cyclization temperature of bpod (136° C.) relative to 8. In contrast, removal of oxygen and methylene carbon atoms from bpod to form the conjugated 1,6-bis(pyridine-3)hex-3-ene-1,5-diyne in which the pyridine rings are adjacent to the alkyne termini restored the high Bergman cyclization temperature (195° C.).

TABLE 1

| Free Ligand | Cyclization Temperature (° C.) |
|---|---|
| 4 | 186 |
| 8 | 149 |
| 9 | 139 |
| 12 | 106 |
| 14 | 100 |

A more pronounced trend was observed between the three compounds in the bis(dimethylamino) to diamino enediyne series (4, 9, 12). Monosubstitution of amino for dimethylamino (9) yielded a dramatic 47° C. decrease in the Bergman cyclization temperature (9=139° C.). Further substitution to form the diamino compound 12 produced an additional 37° C. decrease in the Bergman cyclization temperature. Compound 12 had a thermal cyclization temperature in solution of about 65° C. and 106° C. by DSC as a neat material. It is believed that the enhanced thermal reactivity of 12 results from a combination of the reduced steric hindrance of the primary amine functionalities, as well as an additional contribution from intramolecular hydrogen bonding. Compound 14 exhibited similar reactivity as 12 in the absence of metal (about 55° C. and 100° C. by DSC as a neat material).

In general, both ligands 12 and 14 possessed similar reactivities, were stable in solution for over 24 hours, and could tolerate heating to about 50° C. However, this was not the case in the presence of metals. Upon addition of Zn(II) or Cu(II) to 14, the enediyne turned black instantaneously at room temperature, indicating formation of radical intermediates and subsequent formation of polymeric products. Upon addition of zinc acetate, the reaction was complete in 5 minutes, and reaction completion required 2 hours with no additional heating with the addition of MgCl$_2$.

Figure 6A:
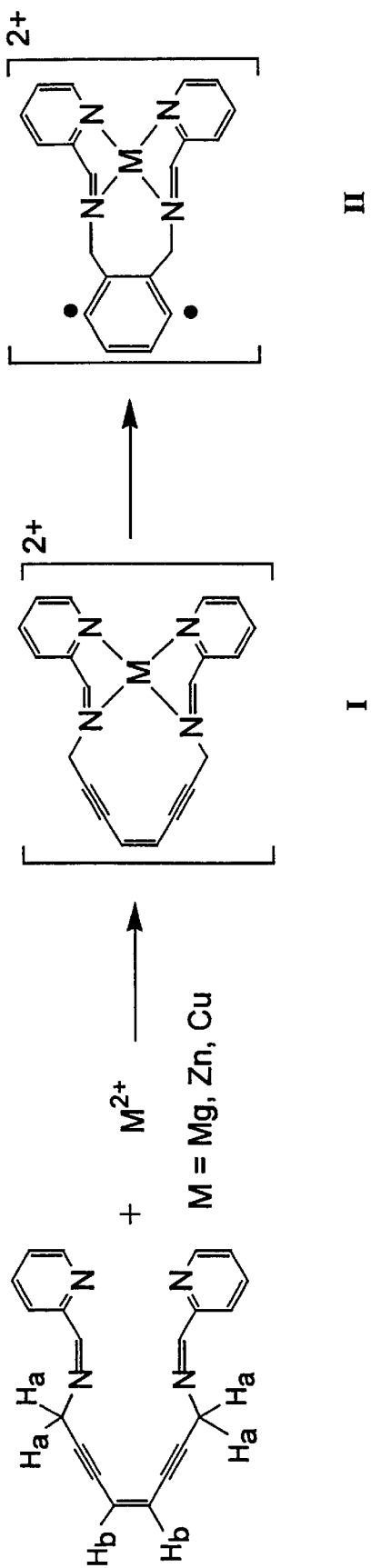
FIG. 6A depicts the reaction scheme of a magnesium complex undergoing Bergman cyclization.
Figure 6B:
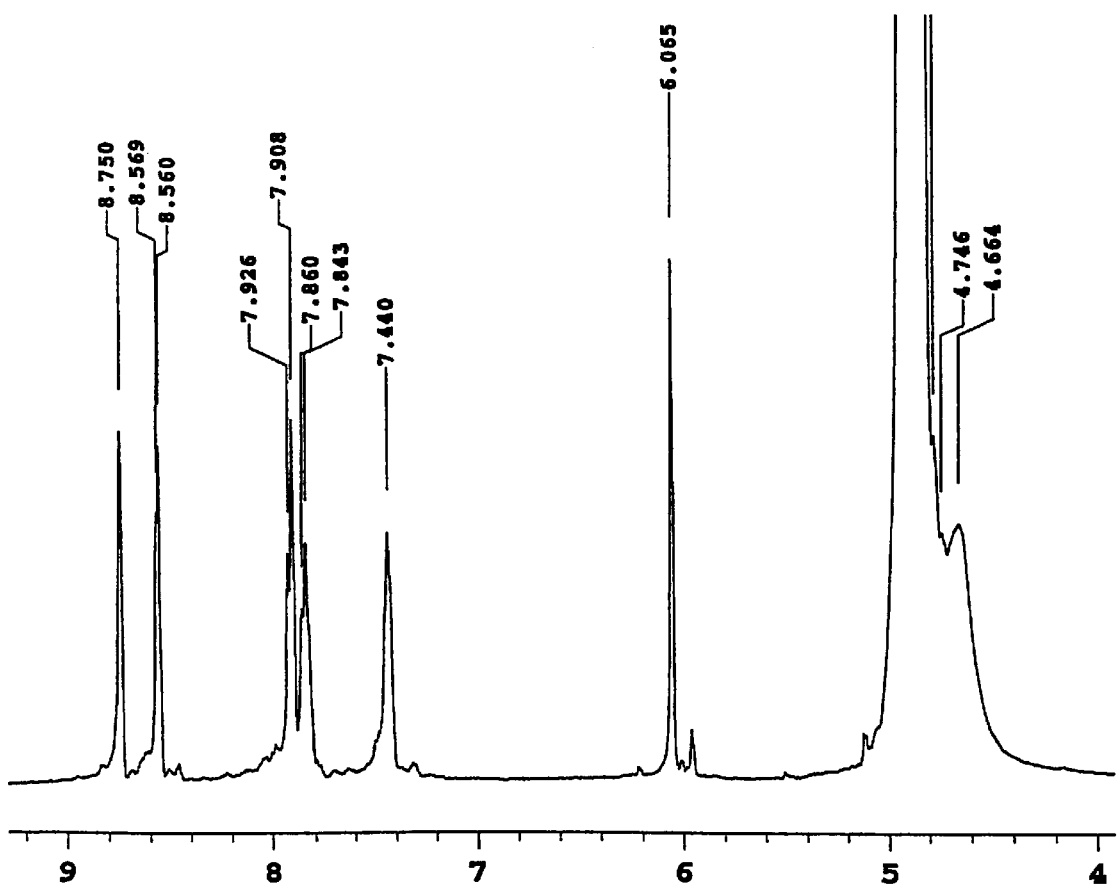
FIG. 6B depicts the $^1$H NMR of I.
Figure 6C:
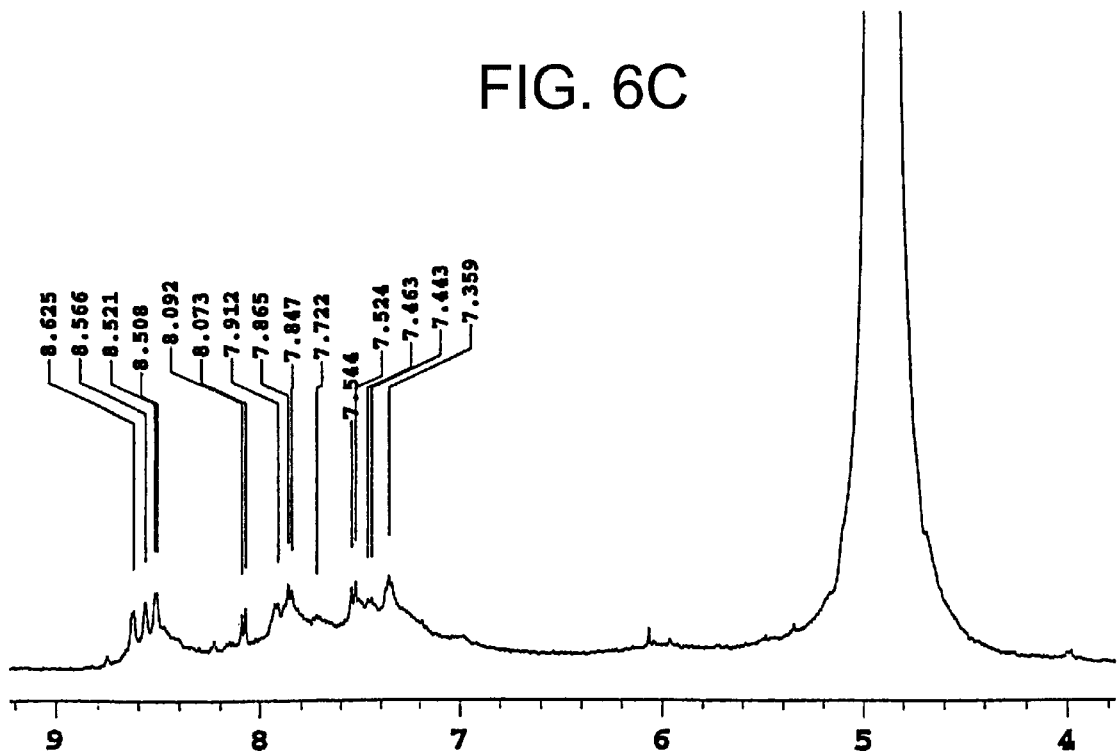
FIG. 6C depicts the $^1$H NMR of II.
Figure 7:
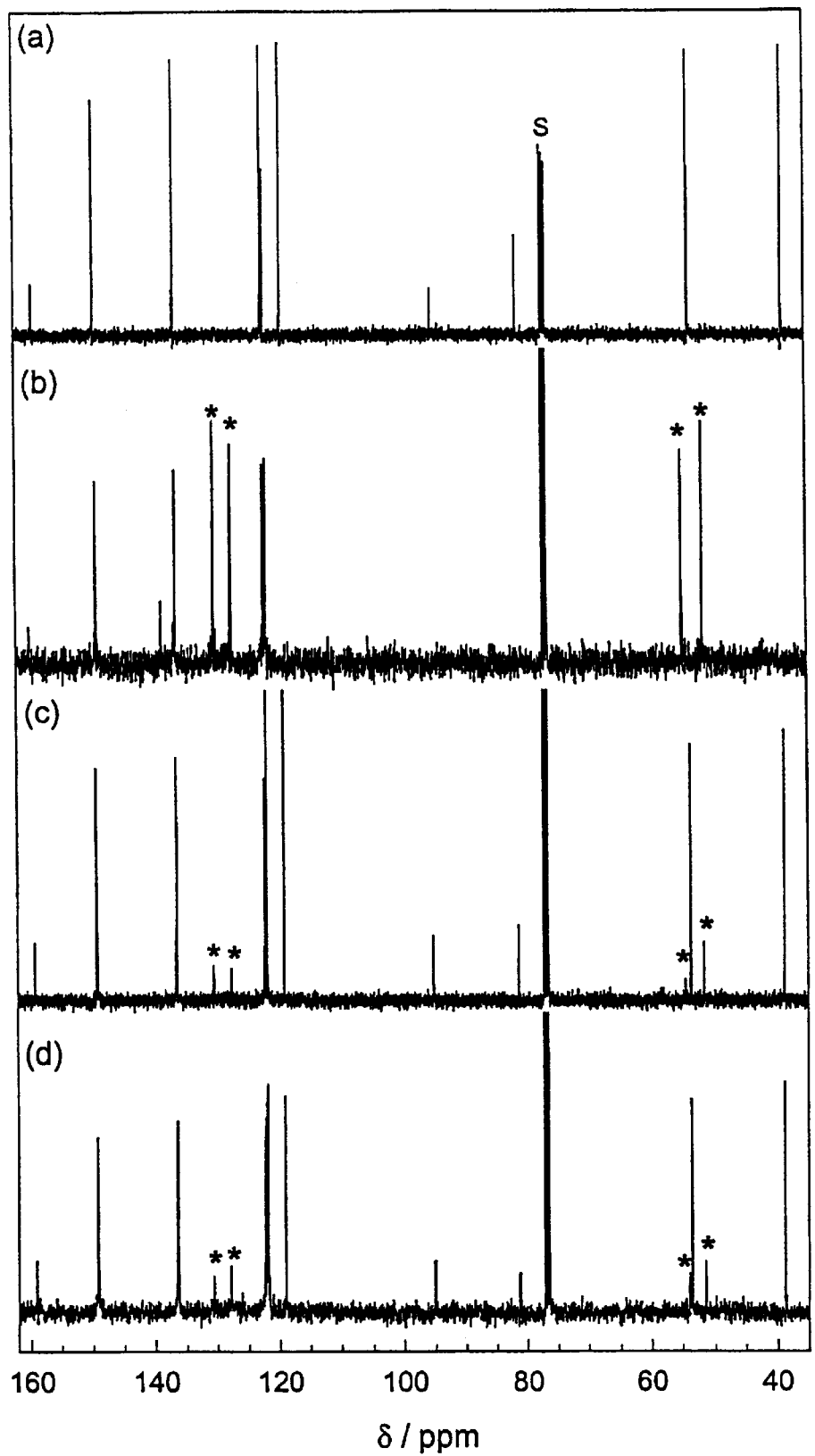
FIG. 7 illustrates the proton decoupled $^{13}$C solution NMR spectra of the product obtained via the ambient temperature cyclization of [Mg(PyimED)]Cl$_2$ (16), the putative Bergman cyclization product obtained via independent synthesis and a mixture thereof with the enediyne starting material, and a partially reacted Bergman cyclization reaction.

The thermal reactivity of 16 was also notable. In methanolic solution containing 20-fold 1,4-cyclohexadiene, warming 16 to room temperature, or addition of Mg$^{2+}$ to 14 led to rapid and pronounced changes in both the $^1$H and {$^1$H} $^{13}$C NMR spectra as depicted in FIGS. 6A, 6B, 6C, and 7. The most diagnostic features were those associated with the —CH$_2$—N═ unit as well as the developing aromatic resonances of the Bergman cyclized product 17 as depicted in FIG. 6C. After warming 16 to room temperature, new resonances were observed at δ 4.99 ppm (ph—CH$_2$—N═) as well as an aromatic multiplet at δ 7.35 ppm in the $^1$H NMR spectrum. The resonances matched very closely with those observed for the uncomplexed benzylimine derivative 5-phenyloxazole-2-carboxaldehyde-N-benzylimine (4.97 ppm), indicating formation of Bergman cyclized product. Since the imine framework was very unstable under these experimental conditions, identification of the reaction product was accomplished by in situ NaBH$_4$ reduction of 17, at 2 h into the reaction, followed by EDTA treatment to generate the more stable demetallated benzylamine 18, as depicted in FIG. 4. Four new singlets were observed in the $^1$H NMR spectrum, two at δ =4.02 (—N—CH$_2$—py) and 3.68 ppm (—CH$_2$—N—) characteristic of the reduced enediyne ligand 15, and two at δ 3.97 (—N—CH$_2$—py) and 3.89 ppm (ph—CH$_2$—N—) deriving from the reduced Bergman cyclized product 18 as depicted in FIG. 6C. These signatures matched those of the literature compound benzyl-pyridin-2-ylmethyl-amine (Boduszek, B. *Tetrahedron*, 52, 12483–12494 (1996)) confirming formation of a benzylamine linkage.

As a control, an authentic sample of the reduced cyclized product 18 was independently synthesized (see Example 7) by reaction of pyridine-2-carboxaldehyde with o-xylene diamine to yield 20, followed by reduction with NaBH$_4$ to give the authentic product 18 (FIG. 5). The independently synthesized reduced product allows $^{13}$C NMR to be used as an additional diagnostic tool for identification of the formation of in situ Bergman enediyne cyclized product. The most prominent differences between the spectra of 15 and 18 derived from the disappearance of the alkyne ($\delta$ 81.5, 95 ppm) and olefin ($\delta$ 119 ppm) carbons, and the appearance of three substituted benzene signals at $\delta$ 127.4, 130.2, and 138.7 ppm. In addition to these diagnostic features, detection of both ph—CH$_2$—N— and —N—CH$_2$—py resonances at 51.4 and 54.0 ppm (Boduszek, B. *Tetrahedron*, 52, 12483–12494 (1996)), respectively, identified the in situ generated Bergman product. Based on the half-life for the reaction (t$_{1/2}$=2.2 h), which was determined from the disappearance of the olefin proton of 16 at $\delta$ 6.06 ppm and the developing ph—CH$_2$—N= signal for 17 at 4.99 ppm, the yield of in situ cyclized product is approximately 40% prior to radical-mediated decomposition.

To estimate the composite $^{13}$C NMR spectrum of the reduced starting material and product, a 2:1 mixture of 15:18 (FIG. 7c) was compared to the in situ thermal Bergman cyclization reaction product (FIG. 7d). Although modest (<0.5 ppm) chemical shift changes were observed due to the presence of radical-mediated decomposition product, the intensities and chemical shifts of the —NCH$_2$—py and ph—CH$_2$—N— resonances ($\delta$ 50–55 ppm), and the substituted benzene signals ($\delta$ 127–131 ppm), correlate well with the 2:1 control mixture of 15:18. Combined, the $^1$H and $^{13}$C NMR data indicate the Mg$^{2+}$-induced formation of Bergman cyclized product 16 occurred at ambient temperature.

EXAMPLE 9

This example illustrates the calculation of the pseudo first-order rate constant and half-life for the reactivity of 12.

To better correlate the thermal reactivity of 12 with that of other enediyne compounds reported in solution, the pseudo first-order rate constant (20-fold cyclohexadiene) and half-life (t$_{1/2}$) were measured for the reactivity of 12 in DMSO by monitoring the disappearance of the —CH— $^1$H NMR resonance at 5.7 ppm at 65° C. A first order plot of ln([12]) versus time (t) and subsequent linear regression (R=0.99) yielded k$_{obs}$=4.16×10$^{-2}$ hours$^{-1}$ and t$_{1/2}$=16.6 hours. As is often observed in solution cyclization reactions of enediynes, a series of products was produced, which in this case included di-substituted benzenes, and as such no dominant species could be isolated from the reaction.

All references, including publications, patent applications, and patents, cited herein are hereby incorporated by reference to the same extent as if each reference there individually and specifically indicated to be incorporated by reference and there set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it there individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of these, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula (I):

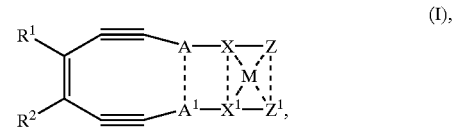

wherein A and A$^1$ are the same or different and each is (CR$^3$R$^4$)$_m$, wherein m is an integer from 0 to 6, and R$^3$ and R$^4$ are the same or different and each is hydrogen, a halo, nitro, cyano, azido, or an organic group selected from the group consisting of linear C$_{1-12}$ alkyl, branched C$_{3-12}$ alkyl, C$_{2-12}$ alkenyl, C$_{3-30}$ cycloalkyl, C$_{3-30}$ heterocycloalkyl, C$_{1-12}$ C$_{5-30}$ heteroaryl, benzylcarbonyl, phenylcarbonyl, and a solubilizing group, wherein the solubilizing group is selected from the group consisting of hydroxyl, an amino, an ammonium salt, a phosphate, a sulfate, a carboxylic acid, and a carboxylic acid salt, wherein the organic group is unsubstituted or substituted with one or more substituents selected from the group consisting of a halo, nitro, cyano, azido, C$_{1-12}$ alkyl, C$_{6-30}$ aryl, and a solubilizing group, wherein the solubilizing group is selected from the group consisting of hydroxyl, an amino, an ammonium salt, a phosphate, a sulfate, a carboxylic acid, and a carboxylic acid salt, wherein the dotted line between A and A$^1$ represents an optional covalent bond linking A and A$^1$ together;

X and X$^1$ are the same or different and each is a substituent selected from the group consisting of an amino, substituted amino, an imino, a N-containing heteroaryl, a N-substituted aryl, and a N-containing heterocycloalkyl, wherein the dotted line between X and X$^1$ represents an optional covalent bond linking X and X$^1$ together;

Z and Z$^1$ are the same or different and each is a substituent selected from the group consisting of an amino, substituted amino, an imino, a N-containing heteroaryl, a N-substituted aryl, and a N-containing heterocycloalkyl, wherein the dotted line between Z and $Z^1$ represents an optional covalent bond linking Z and $Z^1$ together;

$R^1$ and $R^2$ are the same or different and each is hydrogen, linear $C_{1-12}$ alkyl, branched $C_{3-12}$ alkyl, an aralkyl, $C_{6-30}$ aryl, a halo, nitro, or cyano, or $R^1$ and $R^2$, together with the carbons to which they are bonded, comprise $C_{6-30}$ aryl, $C_{3-30}$ heterocycle, or a macrocycle, wherein $R^1$ and $R^2$ are unsubstituted or substituted with one or more substituents selected from the group consisting of a halo, hydroxy, $C_{1-12}$ alkyl, $C_{6-30}$ aryl, alkoxy, nitro, and cyano; and wherein X, $X^1$, Z, and $Z^1$ are capable of forming a tetradentate complex with a metal.

2. The compound of claim 1, further comprising a metal in the form of a tetradentate complex of the formula (II):

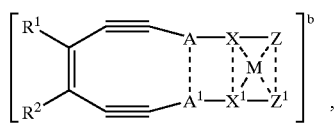
(II)

wherein M is the metal, b represents the charge of the complex and b is an integer ranging from −3 to +3.

3. The compound of claim 2, wherein M is selected from the group consisting of Mg, Ca, Sr, Ba, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Ga, Sn, Pb, Ce, Eu, Gd, Tb, Dy, and Lu.

4. The compound of claim 3, wherein M is selected from the group consisting of Mg, Ca, Gd, Zn, and Cu.

5. The compound of claim 1, wherein at least one of $R^3$ and $R^4$ is an organic group selected from the group consisting of linear $C_{1-12}$ alkyl, branched $C_{3-12}$ alkyl, $C_{2-12}$ alkenyl, $C_{3-30}$ cycloalkyl, $C_{3-30}$ heterocycloalkyl, $C_{6-30}$ aryl, $C_{5-30}$ heteroaryl, benzylcarbonyl, phenylcarbonyl, and a solubilizing group.

6. The compound of claim 5, wherein the organic group is selected from the group consisting of $C_{1-12}$ alkyl or $C_{6-30}$ aryl, wherein the $C_{1-12}$ alkyl or $C_{6-30}$ aryl is unsubstituted or substituted with one or more substituents selected from the group consisting of a halo, nitro, cyano, azido, $C_{1-12}$ alkyl, $C_{6-30}$ aryl, and a solubilizing group.

7. The compound of claim 1, wherein X or $X^1$ comprises a functional selected from the group consisting of:

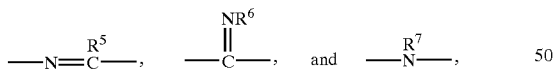

wherein $R^5$, $R^6$, and $R^7$ are each selected from the group consisting of hydrogen, $C_{1-12}$ alkyl, $C_{3-30}$ cycloalkyl, and $C_{6-30}$ aryl.

8. The compound of claim 1, wherein Z and $Z^1$ comprises a functional group selected from the group consisting of amino, $C_{1-12}$ alkylamino, $C_{1-12}$ dialkylamino, anilinyl, pyridinyl, pyrrolyl, pyrrolidinyl, piperdinyl, morpholinyl, imidazolyl, oxazolyl, benzoxazolyl, indolyl, thiazolyl, quinolinyl, isoquinolinyl, pyrazinyl, and quinoxalinyl, wherein Z or $Z^1$ is unsubstituted or substituted with 1 to 3 substituents selected from the group consisting of $C_{1-12}$ alkyl, $C_{1-12}$ alkoxy, $C_{6-30}$ aryl, nitro, cyano, halo, amino, $C_{1-12}$ alkylamino, and $C_{1-12}$ dialkylamino.

9. The compound of claim 1, wherein Z or $Z^1$ is selected from the group consisting of:

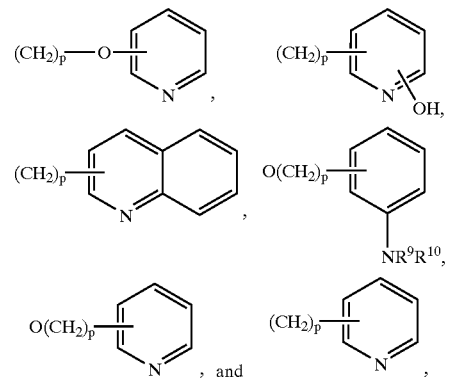

wherein p is an integer from zero to two, wherein $R^9$ and $R^{10}$ are each selected from the group consisting of hydrogen, $C_{1-12}$ alkyl, $C_{3-30}$ cycloalkyl, and $C_{6-30}$ aryl.

10. The compound of claim 1, of the formula (I):

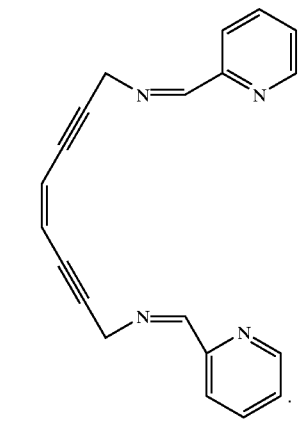

11. The compound of claim 2, of the formula (II):

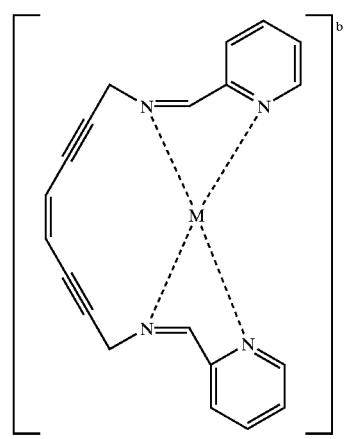

wherein M is selected from the group consisting of Mg, Ca, Sr, Ba, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Ga, Sn, Pb, Ce, Eu, Gd, Tb, Dy, and Lu, b represents the charge of the complex, and b is an integer ranging from −3 to +3.

12. The compound of claim 11, wherein b is +2 and M is selected from the group consisting of Mg, Zn, and Cu.

13. The compound of claim 1, selected from the group consisting of:

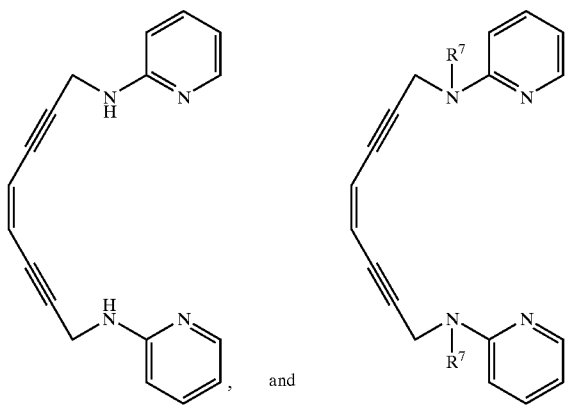

wherein R⁷ is selected from the group consisting of hydrogen, $C_{1-12}$ alkyl, $C_{3-30}$ cycloalkyl, and $C_{6-30}$ aryl.

14. The compound of claim 1, wherein $R^1$ and $R^2$ are selected from the group consisting of hydrogen, linear $C_{1-12}$ alkyl, branched $C_{3-12}$ alkyl, $C_{6-30}$ aryl, and an aralkyl, or $R^1$ and $R^2$, together with the carbons to which they are bonded, comprise a benzene ring.

15. The compound of claim 14, wherein at least one of $R^1$ or $R^2$ is substituted with a substituent selected from the group consisting of a halo, hydroxy, $C_{1-12}$ alkyl, $C_{6-30}$ aryl, alkoxy, nitro, and cyano.

16. The compound of claim 14, wherein $R^1$ and $R^2$ are hydrogen.

17. The compound of claim 2, wherein M is complexed with at least one additional ligand that is capable of complexing with M.

18. The compound of claim 17, wherein the additional ligand is a ligand other than a ligand of the formula (I):

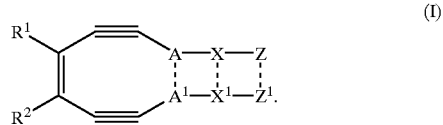

(I)

19. The compound of claim 18, wherein the additional ligand is selected from the group consisting of a halogen-, nitrogen-, oxygen-, sulfur-, and phosphorus-containing functional group.

20. The compound of claim 19, wherein the additional ligand is selected from the group consisting of halo, hydroxy, $C_{1-12}$ alkoxy, thio, $C_{1-12}$ alkylthio, $C_{6-30}$ arylthio, cyano, nitro, amino, $C_{1-12}$ alkylamino, $C_{1-12}$ dialkylamino, phenoxy, anilinyl, $C_{6-30}$ diarylphosphinyl, $C_{1-12}$ dialkylphosphinyl, (alkyl)arylphosphinyl, pyridinyl, pyrrolyl, pyrrolidinyl, piperdinyl, morpholinyl, imidazolyl, oxazolyl, benzofuranyl, benzoxazolyl, indolyl, thiofuranyl, furanyl, thiazolyl, quinolinyl, isoquinolinyl, pyrazinyl, and quinoxalinyl.

21. A pharmaceutical composition comprising a therapeutically effective amount of the compound of claim 2 and a pharmaceutically acceptable carrier.

22. The pharmaceutical composition of claim 21, wherein the therapeutically effective amount is an anticancer effective amount.

23. A method of therapeutically or prophylactically treating cancer in a mammal comprising administering to a mammal in need thereof a therapeutically effective amount of the enediyne tetradentate metal complex of claim 2.

24. The method of claim 23, wherein the complex is capable of forming a benzenoid diradical under physiological conditions.

25. The method of claim 23, wherein the complex forms a benzenoid diradical under photothermal conditions.

26. The method of claim 23, wherein the metal of the enediyne tetradentate metal complex exchanges with a metal in vivo to form a second tetradentate complex, wherein the second tetradentate complex is capable of forming a benzenoid diradical.

27. The method of claim 26, wherein the second tetradentate complex forms a benzenoid diradical under physiological conditions or photothermal conditions.

28. A method of therapeutically or prophylactically treating cancer in a mammal comprising administering to a mammal in need thereof a therapeutically effective amount of the compound of claim 1, wherein the compound forms a tetradentate complex with a metal in vivo and the complex is capable of forming a benzenoid diradical.

29. The method of 28, wherein the metal complex forms a benzenoid diradical under physiological conditions or photothermal conditions.

30. A method of therapeutically or prophylactically treating an infection by a microorganism in a mammal comprising administering to a mammal in need thereof with a therapeutically effective amount of the enediyne tetradentate metal complex of claim 2.

31. The method of claim 30, wherein the complex is capable of forming a benzenoid diradical under physiological conditions.

32. The method of claim 30, wherein the complex forms a benzenoid diradical under photothermal conditions.

33. A method of therapeutically or prophylactically treating a virus in a mammal comprising administering to a mammal in need thereof a therapeutically effective amount of an enediyne tetradentate metal complex of claim 2.

34. The method of claim 33, wherein the complex is capable of forming a benzenoid diradical under physiological conditions.

35. The method of claim 33, wherein the complex forms a benzenoid diradical under photothermal conditions.

* * * * *

UNITED STATES PATENT AND TRADEMARK OFFICE
CERTIFICATE OF CORRECTION

PATENT NO. : 6,514,995 B1
DATED : February 4, 2003
INVENTOR(S) : Zaleski et al.

It is certified that error appears in the above-identified patent and that said Letters Patent is hereby corrected as shown below:

Column 20,
Line 44, "$C_{1-12}$" should read -- $C_{6-30}$ aryl --.

Column 21,
Line 31 "Th" should be corrected to read -- Tb --.
Line 47, "functional selected" should read -- functional group selected --.

UNITED STATES PATENT AND TRADEMARK OFFICE
CERTIFICATE OF CORRECTION

PATENT NO.    : 6,514,995 B1
DATED         : February 4, 2003
INVENTOR(S)   : Zaleski et al.

It is certified that error appears in the above-identified patent and that said Letters Patent is hereby corrected as shown below:

Column 22,
Line 66, should read as follows:
-- The compound of claim 1, selected from the group consisting of:

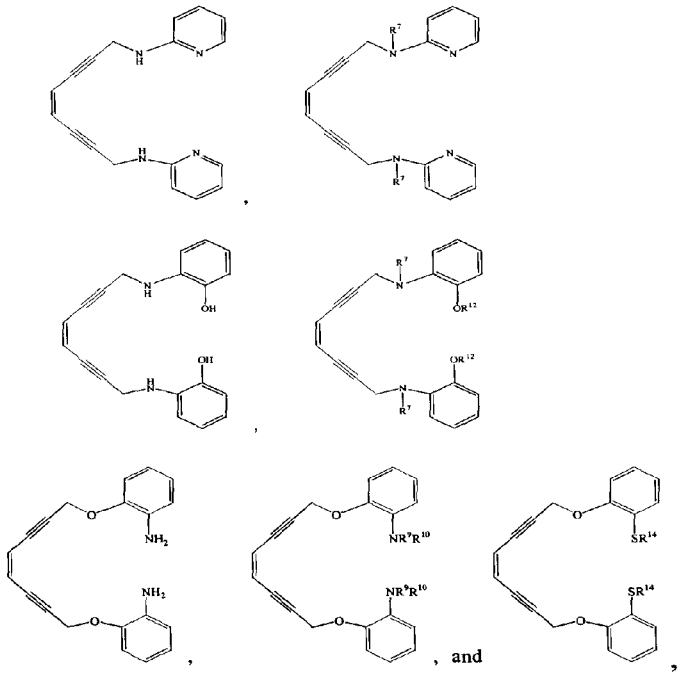

wherein $R^7$, $R^9$, $R^{10}$, $R^{12}$ and $R^{14}$ are each selected from the group consisting of hydrogen $C_{1-12}$ alkyl, $C_{3-30}$ cycloalky, and $C_{6-30}$ aryl. --

Signed and Sealed this

Tenth Day of June, 2003

JAMES E. ROGAN
*Director of the United States Patent and Trademark Office*